US006506892B1

(12) United States Patent
Webb et al.

(10) Patent No.: US 6,506,892 B1
(45) Date of Patent: Jan. 14, 2003

(54) POLYNUCLEOTIDES ENCODING A MYCOPLASMA PROTEIN INVOLVED IN CELL GROWTH REGULATION

(76) Inventors: Andrew C. Webb, 200 Hinckley Rd., Milton, MA (US) 02186; Beverly A. Blazar, 265 Laurel Ave., Providence, RI (US) 02906

( * ) Notice: Subject to any disclaimer, the term of this patent is extended or adjusted under 35 U.S.C. 154(b) by 0 days.

(21) Appl. No.: 09/182,625

(22) Filed: Oct. 29, 1998

Related U.S. Application Data

(60) Provisional application No. 60/063,701, filed on Oct. 29, 1997.

(51) Int. Cl.$^7$ .......................... C07H 21/00; C12N 15/31
(52) U.S. Cl. ........................................... 536/23.7
(58) Field of Search .................. 536/23.7; 530/350, 530/351; 435/69.1

(56) References Cited

PUBLICATIONS

Ambrus, J.L. et al. (1985) "Human B Lymphoma Cell Line Producing B Cell Growth Factor" J. Clin. Invest. 75:732–739.
Bertoglio, Jacques et al. (1989) "Expression and Regulation of Interleukin–1 mRNA and Interleukin–1 Receptors in Human B–Cell Lines" J. Mol. Cell Immunol. 4:139–148.
Bertoglio, J. et al. (1989) "Identification of Interleukin 1α Produced by the 3B6 Human EBV–B Cell Line" Lymphokine Research 8(1):19–24.
Blazar, Beverly A. et al. (1986) "Immunomodulating activity in supernatants from EBV immortalized lymphocytes" Canc. Immunol. 22:62–67.
Blazar, Beverly A. et al. (1983) "Self–stimulating Growth Factor Production by B–Cell Lines Derived from Burkitt's Lymphomas and Other Lines Transformed in Vitro by Epstein–Barr Virus" Can. Res. 43:4562–4568.
Buck, Jochen et al. (1987) "Purification and Biochemical Characterization of a Human Autocrine Growth Factor Produced by Epstein–Barr Virus–Transformed B Cells" J. Immunol. 138(9):2923–2928.
Defrance, T. et al. (1987) "Human Recombinant Interleukin 4 Induces Fce Receptors (CD23) on Normal Human B Lymphocytes" J. Exp. med. 165:1459–1467.
Giovanella, B. et al. (1979) "Growth of Diploid, Epstein–Barr Virus–Carrying Human Lymphoblastoid Cell Lines Heterotransplanted into Nude Mice Under Immunologically Privileged Conditions" Int. J. Cancer 24:103–113.
Gordon, John et al. (1986) "Evidence for an association between CD23 and the receptor for a low molecular weight B cell growth factor" Eur. J. Immunol. 16:1627–1630.
Hall, Robert E. et al. (1996) "cDNA and genomic cloning and expression of the P48 monocytic differentiation/activation factor, a *Mycoplasma fermentans* gene product" Biochem. J. 319:919–927.

Houweling, Ada et al. (1980) "Partial Transformation of Primary Rat Cells by the Leftmost 4.5% Fragment of Adenovirus 5 DNA" Virology 105:537–550.
Muraguchi, A. et al. (1986) "B Cell–Derived BCGF Functions as Autocrine Growth Factor(s) in Normal and Transformed B Lymphocytes" J. Immunol. 137(1):179–186.
Orencole, Scott F. et al. (1989) "Characterization of a Subclone (D10S) of the D10.G4.1 Helper T–Cell Line Which Proliferates to Attomolar Concentrations of Interleukin–1 in the Absence of Mitogens" Cytokine 1(1):14–22.
Rassoulzadegan, Minoo et al. (1982) "The Roles of individual polyoma virus early proteins in oncogenic transformation" Nature 300:713–718.
Swendeman, S. et al. (1987) "The activation antigen BLAST–2, when shed, is an autocrine BCGF for normal and transformed B cells" EMBO J. 6(6):1637–1642.
Tagaya, Y. et al. (1989) "ATL–derived factor (ADF), an IL–2 receptor/Tac inducer homologous to thioredoxin; possible involvement of dithiol–reduction in the IL–2 receptor induction" EMBO J. 8(3):757–764.
Treisman, R. et al. (1981) "Transformation of rat cells by an altered polyoma virus genome expressing only the middle–T protein" Nature 292:595–600.
Uchibayashi, N. et al. (1989) "Recombinant Soluble Fce Receptor II (FceRII/CD23) Has IgE Binding Activity but no B Cell Growth Promoting Activity" J. Immunol. 142:3901–3908.
Wakasugi, H., et al. (1989) "Letter to the Editor" J. Immunol. 142(7):2569–2570.
Wang, F. et al. (1987) "Epstein–Barr virus nuclear antigen 2 specifically induces expression of the B–cell activation antigen CD23" Proc. Natl. Acad. Sci. 84:3452–3456.
M. Matsumoto, Locus D64083, Direct submission to DDBJ/EMBL/GenBank, Sep. 4, 1995. Accessed Sep. 11, 2000.*
M. Matsumoto et al., Nature Medicine 3(11):1266–1270, 1997.*
P. Theiss et al., locus AF100324 Direct submission to GenBank, Apr. 16, 1997. Accessed Sep. 11, 2000.*
P. Theiss et al., J. Bacteriol. 179(12):4013–1022, Jun. 1997.*
G. Rawadi et al., Direct submission to DDBJ/EMBL/GenBank, Sep. 11, 1997. Accessed Sep. 11, 2000.*

* cited by examiner

*Primary Examiner*—Lorraine Spector
(74) *Attorney, Agent, or Firm*—Saliwanchik, Lloyd & Saliwanchik

(57) ABSTRACT

A novel immunoregulatory factor, designated IL-X, is described which has been isolated from Mycoplasma. The subject invention also concerns polynucleotides which encode IL-X. IL-X protein is a growth factor for EBV transformed human B lymphocytes and for murine helper T lymphocytes. Also taught are methods of raising antibodies to IL-X, and cloning of IL-X.

26 Claims, 3 Drawing Sheets

SEQUENCE LISTING

```
<160> NUMBER OF SEQ ID NOS: 16

<210> SEQ ID NO 1
<211> LENGTH: 11
<212> TYPE: PRT
<213> ORGANISM: Mycoplasma fermentans
<220> FEATURE:
<221> NAME/KEY: unsure
<222> LOCATION: 8
<223> OTHER INFORMATION: Peptide

<400> SEQUENCE: 1

Ser Ile Gly Val Ala Glu Asn Xaa Phe Gly Asn
 1               5                  10

<210> SEQ ID NO 2
<211> LENGTH: 17
<212> TYPE: PRT
<213> ORGANISM: Mycoplasma fermentans
<220> FEATURE:
<223> OTHER INFORMATION: Peptide

<400> SEQUENCE: 2
```

Tyr Asn Pro His Val Ile Leu Ser Val Ala Gly Pro Ala Thr Phe Glu
 1               5                  10                  15

Thr

<210> SEQ ID NO 3
<211> LENGTH: 22
<212> TYPE: PRT
<213> ORGANISM: Mycoplasma fermentans
<220> FEATURE:
<223> OTHER INFORMATION: Peptide

<400> SEQUENCE: 3

Val Val Ala Ser Phe Gly Gly Gly Ala Phe Pro Gly Val Thr Thr Phe
 1               5                  10                  15

Asn Glu Gly Phe Asn Gly
            20

<210> SEQ ID NO 4
<211> LENGTH: 10
<212> TYPE: PRT
<213> ORGANISM: Artificial Sequence
<220> FEATURE:
<221> NAME/KEY: unsure
<222> LOCATION: 7
<222> LOCATION: 9
<223> OTHER INFORMATION: Peptide

<400> SEQUENCE: 4

Ile Gly Val Ala Glu Asn Xaa Phe Xaa Asn
 1               5                  10

<210> SEQ ID NO 5
<211> LENGTH: 49
<212> TYPE: DNA
<213> ORGANISM: Artificial Sequence
<220> FEATURE:
<221> NAME/KEY: unsure
<222> LOCATION: 6
<222> LOCATION: 9
<222> LOCATION: 12
<222> LOCATION: 15
<222> LOCATION: 21
<222> LOCATION: 24
<222> LOCATION: 27
<222> LOCATION: 30
<222> LOCATION: 33
<222> LOCATION: 45
<223> OTHER INFORMATION: cDNA

<400> SEQUENCE: 5
ttyggnggng gngcnttycc nggngtnacn acnttyaayg arggnttty                49

<210> SEQ ID NO 6
<211> LENGTH: 166
<212> TYPE: PRT
<213> ORGANISM: Mycoplasma fermentans
<220> FEATURE:
<223> OTHER INFORMATION: Peptide

<400> SEQUENCE: 6

Phe Gly Gly Gly Ala Phe Pro Gly Val Thr Thr Phe Asn Glu Gly Phe
 1               5                  10                  15

Ala Lys Gly Ile Leu Tyr Tyr Asn Gln Lys His Lys Ser Ser Lys Ile
            20                  25                  30

Tyr His Thr Ser Pro Val Lys Leu Asp Ser Gly Phe Thr Ala Gly Glu
            35                  40                  45

Lys Met Asn Thr Val Ile Asn Asn Val Leu Ser Ser Thr Pro Ala Asp
            50                  55                  60

Val Lys Tyr Asn Pro His Val Ile Leu Ser Val Ala Gly Pro Ala Thr
 65                  70                  75                  80

Phe Glu Thr Val Arg Leu Ala Asn Lys Gly Gln Tyr Val Ile Gly Val
                 85                  90                  95

Asp Ser Asp Gln Gly Met Ile Gln Asp Lys Asp Arg Ile Leu Thr Ser
                100                 105                 110

Val Leu Lys His Ile Lys Gln Ala Val Tyr Glu Thr Leu Leu Asp Leu
            115                 120                 125

Ile Leu Glu Lys Glu Glu Gly Tyr Lys Pro Tyr Val Val Lys Asp Lys
        130                 135                 140

Lys Ala Asp Lys Lys Trp Ser His Phe Gly Thr Gln Lys Glu Lys Trp
145                 150                 155                 160

Ile Gly Val Ala Glu Asn
                165

<210> SEQ ID NO 7
<211> LENGTH: 498
<212> TYPE: DNA
<213> ORGANISM: Mycoplasma fermentans
<220> FEATURE:
<223> OTHER INFORMATION: DNA

<400> SEQUENCE: 7
tttggtggag gtgcattccc gggggtgacg acgtttaatg aggggtttgc aaaaggtatt    60
ctatactaca accaaaaaca taaatcaagt aaaatttacc acacatcacc tgttaaatta   120
gactcaggtt ttactgctgg tgaaaaaatg aacactgtta ttaataatgt tttatcttca   180
acaccagctg atgttaaata caacccacat gttatcttat ctgttgctgg acctgctaca   240
tttgaaactg taagattagc aaacaaaggt caatatgtaa ttggtgttga ctcagaccaa   300
ggcatgattc aagacaaaga cagaattctt acatcagttc taaaacacat taaacaagct   360
gtttatgaaa cattattaga tcttattctt gaaaagaag aaggatataa accatatgta    420
gttaaagaca aaaagcaga caaaaaatga agccactttg gaactcaaaa agaaaaatga   480
atcggagtcg ccgaaaac                                                498

<210> SEQ ID NO 8
<211> LENGTH: 1645
<212> TYPE: DNA
<213> ORGANISM: Mycoplasma fermentans
<221> NAME/KEY: CDS
<222> LOCATION: (198)..(1481)

<400> SEQUENCE: 8
aatctcatat tattaataac aaatttaata ttgccacatt ataatttgc acattataaa    60 ctaaaaaatg aaatcacaaa acaaattgca attttttctt attttttgca aaatttgcca   120
ataaaaacca attttgaga tatttaagca aaatatctat ataatgttca atatacaatt   180
aaaaataagg agattat atg aaa aag tca aaa aaa att tta tta gga ttg     230
                   Met Lys Lys Ser Lys Lys Ile Leu Leu Gly Leu
                    1               5                   10 agt cct att gct gct att ctt cct gca gta gct gtt tct tgt gga aac   278
Ser Pro Ile Ala Ala Ile Leu Pro Ala Val Ala Val Ser Cys Gly Asn
            15                  20                  25 aac gat gaa tcc aat att tca ttc aaa gag aaa gat att agt aaa tat   326
Asn Asp Glu Ser Asn Ile Ser Phe Lys Glu Lys Asp Ile Ser Lys Tyr -continued

```
                30                  35                   40
acc aca aca aat gct aat gga aaa caa gtt gtt aaa aac gct gaa ttg      374
Thr Thr Thr Asn Ala Asn Gly Lys Gln Val Val Lys Asn Ala Glu Leu
            45                  50                  55 tta aaa ttg aaa cca att ctt att aca gat gaa ggt aaa att gat gat      422
Leu Lys Leu Lys Pro Ile Leu Ile Thr Asp Glu Gly Lys Ile Asp Asp
60                  65                  70                  75 aaa tca ttt aac caa tca gct ttt gaa gct tta aaa gct ata aat aaa      470
Lys Ser Phe Asn Gln Ser Ala Phe Glu Ala Leu Lys Ala Ile Asn Lys
                80                  85                  90 caa act ggt att gaa att aac aat gtt gaa cct agc tca aac ttt gaa      518
Gln Thr Gly Ile Glu Ile Asn Asn Val Glu Pro Ser Ser Asn Phe Glu
            95                  100                 105 agt gct tac aac agt gca ctt tca gcc gga cac aaa att tga gta ctt      566
Ser Ala Tyr Asn Ser Ala Leu Ser Ala Gly His Lys Ile Trp Val Leu
            110                 115                 120 aat ggc ttc aaa cac caa caa tct att aaa caa tac att gat gct cac      614
Asn Gly Phe Lys His Gln Gln Ser Ile Lys Gln Tyr Ile Asp Ala His
            125                 130                 135 aga gaa gaa ctt gaa aga aat caa atc aaa atc att ggt atc gac ttt      662
Arg Glu Glu Leu Glu Arg Asn Gln Ile Lys Ile Ile Gly Ile Asp Phe
140                 145                 150                 155 gat att gaa aca gag tac aag tga ttc tac tca tta caa ttc aat att      710
Asp Ile Glu Thr Glu Tyr Lys Trp Phe Tyr Ser Leu Gln Phe Asn Ile
                160                 165                 170 aaa gaa tct gca ttt aca aca ggc tat gca att gca agt tga tta agt      758
Lys Glu Ser Ala Phe Thr Thr Gly Tyr Ala Ile Ala Ser Trp Leu Ser
            175                 180                 185 gaa caa gat gaa agt aaa aga gtt gtt gca tca ttt ggt gga ggt gca      806
Glu Gln Asp Glu Ser Lys Arg Val Val Ala Ser Phe Gly Gly Gly Ala
            190                 195                 200 ttc cca ggt gtt aca aca ttt aac gaa ggt ttt gca aaa ggt att cta      854
Phe Pro Gly Val Thr Thr Phe Asn Glu Gly Phe Ala Lys Gly Ile Leu
            205                 210                 215 tac tac aac caa aaa cat aaa tca agt aaa att tac cac aca tca cct      902
Tyr Tyr Asn Gln Lys His Lys Ser Ser Lys Ile Tyr His Thr Ser Pro
220                 225                 230                 235 gtt aaa tta gac tca ggt ttt act gct ggt gaa aaa atg aac act gtt      950
Val Lys Leu Asp Ser Gly Phe Thr Ala Gly Glu Lys Met Asn Thr Val
            240                 245                 250 att aat aat gtt tta tct tca aca cca gct gat gtt aaa tac aac cca      998
Ile Asn Asn Val Leu Ser Ser Thr Pro Ala Asp Val Lys Tyr Asn Pro
            255                 260                 265 cat gtt atc tta tct gtt gct gga cct gct aca ttt gaa act gta aga     1046
His Val Ile Leu Ser Val Ala Gly Pro Ala Thr Phe Glu Thr Val Arg
            270                 275                 280 tta gca aac aaa ggt caa tat gta att ggt gtt gac tca gac caa ggc     1094
Leu Ala Asn Lys Gly Gln Tyr Val Ile Gly Val Asp Ser Asp Gln Gly
            285                 290                 295 atg att caa gac aaa gac aga att ctt aca tca gtt cta aaa cac att     1142
Met Ile Gln Asp Lys Asp Arg Ile Leu Thr Ser Val Leu Lys His Ile
300                 305                 310                 315 aaa caa gct gtt tat gaa aca tta tta gat ctt att ctt gaa aaa gaa     1190
Lys Gln Ala Val Tyr Glu Thr Leu Leu Asp Leu Ile Leu Glu Lys Glu
            320                 325                 330 gaa gga tat aaa cca tat gta gtt aaa gac aaa aaa gca gac aaa aaa     1238
Glu Gly Tyr Lys Pro Tyr Val Val Lys Asp Lys Lys Ala Asp Lys Lys
            335                 340                 345 tga agc cac ttt gga act caa aaa gaa aaa tga atc ggt gtc gca gaa     1286
```

```
Trp Ser His Phe Gly Thr Gln Lys Glu Lys Trp Ile Gly Val Ala Glu
            350                 355                 360 aac cac ttc tca aat aca gaa gaa caa gca aaa att aat aac aaa att    1334
Asn His Phe Ser Asn Thr Glu Glu Gln Ala Lys Ile Asn Asn Lys Ile
        365                 370                 375 aaa gaa gca att aaa atg ttt aaa gaa tta cca gaa gat ttc gtt aaa    1382
Lys Glu Ala Ile Lys Met Phe Lys Glu Leu Pro Glu Asp Phe Val Lys
380                 385                 390                 395 tat att aat agt gac aaa gct tta aaa gat ggt aat aaa att gac aat    1430
Tyr Ile Asn Ser Asp Lys Ala Leu Lys Asp Gly Asn Lys Ile Asp Asn
                400                 405                 410 gtt agt gaa aga tta gaa gca att att tct gct att aat aag gca gca    1478
Val Ser Glu Arg Leu Glu Ala Ile Ile Ser Ala Ile Asn Lys Ala Ala
            415                 420                 425 aaa taattaatca aaaaaatgct ggaaaatatc cagcatttt tattttaaat          1531
Lys atgaaaaaag tatattttt tgttaatttt tgaagaaatt agataaaaca gttttccgt    1591 ttttgtcttc aaataagata aataagagaa aaaggttgt aaaactgcct aaga         1645

<210> SEQ ID NO 9
<211> LENGTH: 428
<212> TYPE: PRT
<213> ORGANISM: Mycoplasma fermentans

<400> SEQUENCE: 9

Met Lys Lys Ser Lys Lys Ile Leu Leu Gly Leu Ser Pro Ile Ala Ala
1               5                   10                  15

Ile Leu Pro Ala Val Ala Val Ser Cys Gly Asn Asn Asp Glu Ser Asn
            20                  25                  30

Ile Ser Phe Lys Glu Lys Asp Ile Ser Lys Tyr Thr Thr Thr Asn Ala
        35                  40                  45

Asn Gly Lys Gln Val Val Lys Asn Ala Glu Leu Leu Lys Leu Lys Pro
    50                  55                  60

Ile Leu Ile Thr Asp Glu Gly Ile Asp Asp Lys Ser Phe Asn Gln
65                  70                  75                  80

Ser Ala Phe Glu Ala Leu Lys Ala Ile Asn Lys Gln Thr Gly Ile Glu
                85                  90                  95

Ile Asn Asn Val Glu Pro Ser Ser Asn Phe Glu Ser Ala Tyr Asn Ser
            100                 105                 110

Ala Leu Ser Ala Gly His Lys Ile Trp Val Leu Asn Gly Phe Lys His
        115                 120                 125

Gln Gln Ser Ile Lys Gln Tyr Ile Asp Ala His Arg Glu Glu Leu Glu
    130                 135                 140

Arg Asn Gln Ile Lys Ile Ile Gly Ile Asp Phe Asp Ile Glu Thr Glu
145                 150                 155                 160

Tyr Lys Trp Phe Tyr Ser Leu Gln Phe Asn Ile Lys Glu Ser Ala Phe
                165                 170                 175

Thr Thr Gly Tyr Ala Ile Ala Ser Trp Leu Ser Glu Gln Asp Glu Ser
            180                 185                 190

Lys Arg Val Val Ala Ser Phe Gly Gly Ala Phe Pro Gly Val Thr
        195                 200                 205

Thr Phe Asn Glu Gly Phe Ala Lys Gly Ile Leu Tyr Tyr Asn Gln Lys
    210                 215                 220

His Lys Ser Ser Lys Ile Tyr His Thr Ser Pro Val Lys Leu Asp Ser
225                 230                 235                 240
```

```
Gly Phe Thr Ala Gly Glu Lys Met Asn Thr Val Ile Asn Asn Val Leu
                245                 250                 255

Ser Ser Thr Pro Ala Asp Val Lys Tyr Asn Pro His Val Ile Leu Ser
                260                 265                 270

Val Ala Gly Pro Ala Thr Phe Glu Thr Val Arg Leu Ala Asn Lys Gly
                275                 280                 285

Gln Tyr Val Ile Gly Val Asp Ser Asp Gln Gly Met Ile Gln Asp Lys
                290                 295                 300

Asp Arg Ile Leu Thr Ser Val Leu Lys His Ile Lys Gln Ala Val Tyr
305                 310                 315                 320

Glu Thr Leu Leu Asp Leu Ile Leu Glu Lys Glu Gly Tyr Lys Pro
                325                 330                 335

Tyr Val Val Lys Asp Lys Ala Asp Lys Lys Trp Ser His Phe Gly
                340                 345                 350

Thr Gln Lys Glu Lys Trp Ile Gly Val Ala Glu Asn His Phe Ser Asn
                355                 360                 365

Thr Glu Glu Gln Ala Lys Ile Asn Asn Lys Ile Lys Glu Ala Ile Lys
                370                 375                 380

Met Phe Lys Glu Leu Pro Glu Asp Phe Val Lys Tyr Ile Asn Ser Asp
385                 390                 395                 400

Lys Ala Leu Lys Asp Gly Asn Lys Ile Asp Asn Val Ser Glu Arg Leu
                405                 410                 415

Glu Ala Ile Ile Ser Ala Ile Asn Lys Ala Ala Lys
                420                 425

<210> SEQ ID NO 10
<211> LENGTH: 11
<212> TYPE: PRT
<213> ORGANISM: Mycoplasma fermentans

<400> SEQUENCE: 10

Trp Ile Gly Val Ala Glu Asn His Phe Ser Asn
1               5                   10

<210> SEQ ID NO 11
<211> LENGTH: 22
<212> TYPE: PRT
<213> ORGANISM: Mycoplasma fermentans

<400> SEQUENCE: 11

Val Val Ala Ser Phe Gly Gly Gly Ala Phe Pro Gly Val Thr Thr Phe
1               5                   10                  15

Asn Glu Gly Phe Ala Lys
                20

<210> SEQ ID NO 12
<211> LENGTH: 7
<212> TYPE: PRT
<213> ORGANISM: Artificial Sequence
<220> FEATURE:
<223> OTHER INFORMATION: Consensus sequence for prokaryotic signal
      peptidase II

<400> SEQUENCE: 12

Val Ala Val Ser Cys Gly Asn
1               5

<210> SEQ ID NO 13
<211> LENGTH: 1645
<212> TYPE: DNA
```

-continued

```
<213> ORGANISM: Mycoplasma fermentans
<221> NAME/KEY: CDS
<222> LOCATION: (198)..(1481)

<400> SEQUENCE: 13
aatctcatat tattaataac aaatttaata ttgccacatt ataattttgc acattataaa      60
ctaaaaaatg aaatcacaaa acaaattgca attttttctt atttttttgca aaatttgcca    120 ataaaaacca attttgaga tatttaagca aaatatctat ataatgttca atatacaatt     180
aaaaataagg agattat atg aaa aag tca aaa aaa att tta tta gga ttg       230
                   Met Lys Lys Ser Lys Lys Ile Leu Leu Gly Leu
                    1               5                  10 agt cct att gct gct att ctt cct gca gta gct gtt tct tgt gga aac     278
Ser Pro Ile Ala Ala Ile Leu Pro Ala Val Ala Val Ser Cys Gly Asn
             15                  20                  25 aac gat gaa tcc aat att tca ttc aaa gag aaa gat att agt aaa tat     326
Asn Asp Glu Ser Asn Ile Ser Phe Lys Glu Lys Asp Ile Ser Lys Tyr
         30                  35                  40 acc aca aca aat gct aat gga aaa caa gtt gtt aaa aac gct gaa ttg     374
Thr Thr Thr Asn Ala Asn Gly Lys Gln Val Val Lys Asn Ala Glu Leu
     45                  50                  55 tta aaa ttg aaa cca att ctt att aca gat gaa ggt aaa att gat gat     422
Leu Lys Leu Lys Pro Ile Leu Ile Thr Asp Glu Gly Lys Ile Asp Asp
 60                  65                  70                  75 aaa tca ttt aac caa tca gct ttt gaa gct tta aaa gct ata aat aaa     470
Lys Ser Phe Asn Gln Ser Ala Phe Glu Ala Leu Lys Ala Ile Asn Lys
                 80                  85                  90 caa act ggt att gaa att aac aat gtt gaa cct agc tca aac ttt gaa     518
Gln Thr Gly Ile Glu Ile Asn Asn Val Glu Pro Ser Ser Asn Phe Glu
             95                 100                 105 agt gct tac aac agt gca ctt tca gcc gga cac aaa att tga gta ctt     566
Ser Ala Tyr Asn Ser Ala Leu Ser Ala Gly His Lys Ile Trp Val Leu
        110                 115                 120 aat ggc ttc aaa cac caa caa tct att aaa caa tac att gat gct tac     614
Asn Gly Phe Lys His Gln Gln Ser Ile Lys Gln Tyr Ile Asp Ala Tyr
    125                 130                 135 aga gaa gaa ctt gaa aga aat caa atc aaa atc att ggt atc gac ttt     662
Arg Glu Glu Leu Glu Arg Asn Gln Ile Lys Ile Ile Gly Ile Asp Phe
140                 145                 150                 155 gat att gaa aca gag tac aag tga ttc tac tca tta caa ttc aat att     710
Asp Ile Glu Thr Glu Tyr Lys Trp Phe Tyr Ser Leu Gln Phe Asn Ile
                160                 165                 170 aaa gaa tct gca ttt aca aca ggc tat gca att gca agt tga tta agt     758
Lys Glu Ser Ala Phe Thr Thr Gly Tyr Ala Ile Ala Ser Trp Leu Ser
            175                 180                 185 gaa caa gat gaa agt aaa aga gtt gtt gca tca ttt ggt gga ggt gca     806
Glu Gln Asp Glu Ser Lys Arg Val Val Ala Ser Phe Gly Gly Gly Ala
        190                 195                 200 ttc cca ggt gtt aca aca ttt aac gaa ggt ttt gca aaa ggt att cta     854
Phe Pro Gly Val Thr Thr Phe Asn Glu Gly Phe Ala Lys Gly Ile Leu
    205                 210                 215 tac tac aac caa aaa cat aaa tca agt aaa att tac cac aca tca cct     902
Tyr Tyr Asn Gln Lys His Lys Ser Ser Lys Ile Tyr His Thr Ser Pro
220                 225                 230                 235 gtt aaa tta gac tca ggt ttt act gct ggt gaa aaa atg aac act gtt     950
Val Lys Leu Asp Ser Gly Phe Thr Ala Gly Glu Lys Met Asn Thr Val
                240                 245                 250 att aat aat gtt tta tct tca aca cca gct gat gtt aaa tac aac cca     998
Ile Asn Asn Val Leu Ser Ser Thr Pro Ala Asp Val Lys Tyr Asn Pro
            255                 260                 265
```

-continued

```
cat gtt atc tta tct gtt gct gga cct gct aca ttt gaa act gta aga    1046
His Val Ile Leu Ser Val Ala Gly Pro Ala Thr Phe Glu Thr Val Arg
        270                 275                 280 tta gca aac aaa ggt caa tat gta att ggt gtt gac tca gac caa ggc    1094
Leu Ala Asn Lys Gly Gln Tyr Val Ile Gly Val Asp Ser Asp Gln Gly
    285                 290                 295 atg att caa gac aaa gac aga att ctt aca tca gtt cta aaa cac att    1142
Met Ile Gln Asp Lys Asp Arg Ile Leu Thr Ser Val Leu Lys His Ile
300                 305                 310                 315 aaa caa gct gtt tat gaa aca tta tta gat ctt att ctt gaa aaa gaa    1190
Lys Gln Ala Val Tyr Glu Thr Leu Leu Asp Leu Ile Leu Glu Lys Glu
                320                 325                 330 gaa gga tat aaa cca tat gta gtt aaa gac aaa aaa gca gac aaa aaa    1238
Glu Gly Tyr Lys Pro Tyr Val Val Lys Asp Lys Lys Ala Asp Lys Lys
            335                 340                 345 tga agc cac ttt gga act caa aaa gaa aaa tga atc ggt gtc gca gaa    1286
Trp Ser His Phe Gly Thr Gln Lys Glu Lys Trp Ile Gly Val Ala Glu
        350                 355                 360 aac cac ttc tca aat aca gaa gaa caa gca aaa att aat aac aaa att    1334
Asn His Phe Ser Asn Thr Glu Glu Gln Ala Lys Ile Asn Asn Lys Ile
    365                 370                 375 aaa gaa gca att aaa atg ttt aaa gaa tta cca gaa gat ttc gtt aaa    1382
Lys Glu Ala Ile Lys Met Phe Lys Glu Leu Pro Glu Asp Phe Val Lys
380                 385                 390                 395 tat att aat agt gac aaa gct tta aaa gat ggt aat aaa att gac aat    1430
Tyr Ile Asn Ser Asp Lys Ala Leu Lys Asp Gly Asn Lys Ile Asp Asn
                400                 405                 410 gtt agt gaa aga tta gaa gca att att tct gct att aat aag gca gca    1478
Val Ser Glu Arg Leu Glu Ala Ile Ile Ser Ala Ile Asn Lys Ala Ala
            415                 420                 425 aaa taattaatca aaaaaatgct ggaaaatatc cagcattttt tattttaaat        1531
Lys atgaaaaaag tatattttt tgttaatttt tgaagaaatt agataaaaca gttttttccgt  1591 ttttgtcttc aaataagata aataagagaa aaaggttgt aaaactgcct aaga         1645
```

<210> SEQ ID NO 14
<211> LENGTH: 404
<212> TYPE: PRT
<213> ORGANISM: Mycoplasma fermentans

<400> SEQUENCE: 14

```
Cys Gly Asn Asn Asp Glu Ser Asn Ile Ser Phe Lys Glu Lys Asp Ile
 1               5                  10                  15

Ser Lys Tyr Thr Thr Thr Asn Ala Asn Gly Lys Gln Val Val Lys Asn
            20                  25                  30

Ala Glu Leu Leu Lys Leu Lys Pro Ile Leu Ile Thr Asp Glu Gly Lys
        35                  40                  45

Ile Asp Asp Lys Ser Phe Asn Gln Ser Ala Phe Glu Ala Leu Lys Ala
    50                  55                  60

Ile Asn Lys Gln Thr Gly Ile Glu Ile Asn Asn Val Glu Pro Ser Ser
65                  70                  75                  80

Asn Phe Glu Ser Ala Tyr Asn Ser Ala Leu Ser Ala Gly His Lys Ile
                85                  90                  95

Trp Val Leu Asn Gly Phe Lys His Gln Gln Ser Ile Lys Gln Tyr Ile
            100                 105                 110

Asp Ala His Arg Glu Glu Leu Glu Arg Asn Gln Ile Lys Ile Ile Gly
        115                 120                 125
```

-continued

Ile Asp Phe Asp Ile Glu Thr Glu Tyr Lys Trp Phe Tyr Ser Leu Gln
130                 135                 140

Phe Asn Ile Lys Glu Ser Ala Phe Thr Thr Gly Tyr Ala Ile Ala Ser
145                 150                 155                 160

Trp Leu Ser Glu Gln Asp Glu Ser Lys Arg Val Val Ala Ser Phe Gly
        165                 170                 175

Gly Gly Ala Phe Pro Gly Val Thr Thr Phe Asn Glu Gly Phe Ala Lys
        180                 185                 190

Gly Ile Leu Tyr Tyr Asn Gln Lys His Lys Ser Ser Lys Ile Tyr His
        195                 200                 205

Thr Ser Pro Val Lys Leu Asp Ser Gly Phe Thr Ala Gly Glu Lys Met
210                 215                 220

Asn Thr Val Ile Asn Asn Val Leu Ser Ser Thr Pro Ala Asp Val Lys
225                 230                 235                 240

Tyr Asn Pro His Val Ile Leu Ser Val Ala Gly Pro Ala Thr Phe Glu
                245                 250                 255

Thr Val Arg Leu Ala Asn Lys Gly Gln Tyr Val Ile Gly Val Asp Ser
            260                 265                 270

Asp Gln Gly Met Ile Gln Asp Lys Asp Arg Ile Leu Thr Ser Val Leu
        275                 280                 285

Lys His Ile Lys Gln Ala Val Tyr Glu Thr Leu Leu Asp Leu Ile Leu
        290                 295                 300

Glu Lys Glu Glu Gly Tyr Lys Pro Tyr Val Val Lys Asp Lys Lys Ala
305                 310                 315                 320

Asp Lys Lys Trp Ser His Phe Gly Thr Gln Lys Glu Lys Trp Ile Gly
                325                 330                 335

Val Ala Glu Asn His Phe Ser Asn Thr Glu Glu Gln Ala Lys Ile Asn
            340                 345                 350

Asn Lys Ile Lys Glu Ala Ile Lys Met Phe Lys Glu Leu Pro Glu Asp
        355                 360                 365

Phe Val Lys Tyr Ile Asn Ser Asp Lys Ala Leu Lys Asp Gly Asn Lys
        370                 375                 380

Ile Asp Asn Val Ser Glu Arg Leu Glu Ala Ile Ile Ser Ala Ile Asn
385                 390                 395                 400

Lys Ala Ala Lys

<210> SEQ ID NO 15
<211> LENGTH: 404
<212> TYPE: PRT
<213> ORGANISM: Mycoplasma fermentans

<400> SEQUENCE: 15

Cys Gly Asn Asn Asp Glu Ser Asn Ile Ser Phe Lys Glu Lys Asp Ile
1               5                   10                  15

Ser Lys Tyr Thr Thr Asn Ala Asn Gly Lys Gln Val Val Lys Asn
            20                  25                  30

Ala Glu Leu Leu Lys Leu Lys Pro Ile Leu Ile Thr Asp Glu Gly Lys
        35                  40                  45

Ile Asp Asp Lys Ser Phe Asn Gln Ser Ala Phe Glu Ala Leu Lys Ala
    50                  55                  60

Ile Asn Lys Gln Thr Gly Ile Glu Ile Asn Asn Val Glu Pro Ser Ser
65                  70                  75                  80

Asn Phe Glu Ser Ala Tyr Asn Ser Ala Leu Ser Ala Gly His Lys Ile
                85                  90                  95

-continued

```
Trp Val Leu Asn Gly Phe Lys His Gln Gln Ser Ile Lys Gln Tyr Ile
            100                 105                 110

Asp Ala Tyr Arg Glu Glu Leu Glu Arg Asn Gln Ile Lys Ile Ile Gly
        115                 120                 125

Ile Asp Phe Asp Ile Glu Thr Glu Tyr Lys Trp Phe Tyr Ser Leu Gln
    130                 135                 140

Phe Asn Ile Lys Glu Ser Ala Phe Thr Thr Gly Tyr Ala Ile Ala Ser
145                 150                 155                 160

Trp Leu Ser Glu Gln Asp Glu Ser Lys Arg Val Val Ala Ser Phe Gly
                165                 170                 175

Gly Gly Ala Phe Pro Gly Val Thr Thr Phe Asn Glu Gly Phe Ala Lys
            180                 185                 190

Gly Ile Leu Tyr Tyr Asn Gln Lys His Lys Ser Ser Lys Ile Tyr His
        195                 200                 205

Thr Ser Pro Val Lys Leu Asp Ser Gly Phe Thr Ala Gly Glu Lys Met
    210                 215                 220

Asn Thr Val Ile Asn Asn Val Leu Ser Ser Thr Pro Ala Asp Val Lys
225                 230                 235                 240

Tyr Asn Pro His Val Ile Leu Ser Val Ala Gly Pro Ala Thr Phe Glu
                245                 250                 255

Thr Val Arg Leu Ala Asn Lys Gly Gln Tyr Val Ile Gly Val Asp Ser
            260                 265                 270

Asp Gln Gly Met Ile Gln Asp Lys Asp Arg Ile Leu Thr Ser Val Leu
        275                 280                 285

Lys His Ile Lys Gln Ala Val Tyr Glu Thr Leu Leu Asp Leu Ile Leu
    290                 295                 300

Glu Lys Glu Glu Gly Tyr Lys Pro Tyr Val Val Lys Asp Lys Lys Ala
305                 310                 315                 320

Asp Lys Lys Trp Ser His Phe Gly Thr Gln Lys Glu Lys Trp Ile Gly
                325                 330                 335

Val Ala Glu Asn His Phe Ser Asn Thr Glu Glu Gln Ala Lys Ile Asn
            340                 345                 350

Asn Lys Ile Lys Glu Ala Ile Lys Met Phe Lys Glu Leu Pro Glu Asp
        355                 360                 365

Phe Val Lys Tyr Ile Asn Ser Asp Lys Ala Leu Lys Asp Gly Asn Lys
    370                 375                 380

Ile Asp Asn Val Ser Glu Arg Leu Glu Ala Ile Ile Ser Ala Ile Asn
385                 390                 395                 400

Lys Ala Ala Lys

<210> SEQ ID NO 16
<211> LENGTH: 428
<212> TYPE: PRT
<213> ORGANISM: Mycoplasma fermentans

<400> SEQUENCE: 16

Met Lys Lys Ser Lys Lys Ile Leu Leu Gly Leu Ser Pro Ile Ala Ala
  1               5                  10                  15

Ile Leu Pro Ala Val Ala Val Ser Cys Gly Asn Asn Asp Glu Ser Asn
             20                  25                  30

Ile Ser Phe Lys Glu Lys Asp Ile Ser Lys Tyr Thr Thr Thr Asn Ala
         35                  40                  45

Asn Gly Lys Gln Val Val Lys Asn Ala Glu Leu Leu Lys Leu Lys Pro
     50                  55                  60
```

-continued

```
Ile Leu Ile Thr Asp Glu Gly Lys Ile Asp Lys Ser Phe Asn Gln
65                  70                  75                  80

Ser Ala Phe Glu Ala Leu Lys Ala Ile Asn Lys Gln Thr Gly Ile Glu
                85                  90                  95

Ile Asn Asn Val Glu Pro Ser Ser Asn Phe Glu Ser Ala Tyr Asn Ser
                100                 105                 110

Ala Leu Ser Ala Gly His Lys Ile Trp Val Leu Asn Gly Phe Lys His
            115                 120                 125

Gln Gln Ser Ile Lys Gln Tyr Ile Asp Ala Tyr Arg Glu Glu Leu Glu
        130                 135                 140

Arg Asn Gln Ile Lys Ile Ile Gly Ile Asp Phe Asp Ile Glu Thr Glu
145                 150                 155                 160

Tyr Lys Trp Phe Tyr Ser Leu Gln Phe Asn Ile Lys Glu Ser Ala Phe
                165                 170                 175

Thr Thr Gly Tyr Ala Ile Ala Ser Trp Leu Ser Glu Gln Asp Glu Ser
                180                 185                 190

Lys Arg Val Val Ala Ser Phe Gly Gly Ala Phe Pro Gly Val Thr
        195                 200                 205

Thr Phe Asn Glu Gly Phe Ala Lys Gly Ile Leu Tyr Tyr Asn Gln Lys
        210                 215                 220

His Lys Ser Ser Lys Ile Tyr His Thr Ser Pro Val Lys Leu Asp Ser
225                 230                 235                 240

Gly Phe Thr Ala Gly Glu Lys Met Asn Thr Val Ile Asn Asn Val Leu
                245                 250                 255

Ser Ser Thr Pro Ala Asp Val Lys Tyr Asn Pro His Val Ile Leu Ser
                260                 265                 270

Val Ala Gly Pro Ala Thr Phe Glu Thr Val Arg Leu Ala Asn Lys Gly
            275                 280                 285

Gln Tyr Val Ile Gly Val Asp Ser Asp Gln Gly Met Ile Gln Asp Lys
        290                 295                 300

Asp Arg Ile Leu Thr Ser Val Leu Lys His Ile Lys Gln Ala Val Tyr
305                 310                 315                 320

Glu Thr Leu Leu Asp Leu Ile Leu Glu Lys Glu Glu Gly Tyr Lys Pro
                325                 330                 335

Tyr Val Val Lys Asp Lys Lys Ala Asp Lys Lys Trp Ser His Phe Gly
                340                 345                 350

Thr Gln Lys Glu Lys Trp Ile Gly Val Ala Glu Asn His Phe Ser Asn
        355                 360                 365

Thr Glu Glu Gln Ala Lys Ile Asn Asn Lys Ile Lys Glu Ala Ile Lys
    370                 375                 380

Met Phe Lys Glu Leu Pro Glu Asp Phe Val Lys Tyr Ile Asn Ser Asp
385                 390                 395                 400

Lys Ala Leu Lys Asp Gly Asn Lys Ile Asp Asn Val Ser Glu Arg Leu
                405                 410                 415

Glu Ala Ile Ile Ser Ala Ile Asn Lys Ala Ala Lys
                420                 425
```

POLYNUCLEOTIDES ENCODING A MYCOPLASMA PROTEIN INVOLVED IN CELL GROWTH REGULATION

CROSS-REFERENCE TO RELATED APPLICATIONS

This application claims the benefit of U.S. Provisional Application No. 60/063,701 filed Oct. 29, 1997.

BACKGROUND OF THE INVENTION

Epstein-Barr Virus (EBV) is a lymphotropic virus in humans that is closely associated with two malignancies, Burkitt's lymphoma, and nasopharyngeal carcinoma, as well as a lymphoproliferative disorder, infectious mononucleosis. Also, in recent years, several EBV-associated proliferative syndromes and malignancies have been described in the profoundly immunocompromised host.

There are two main types of EBV carrying B lymphocyte lines, i.e., Burkitt's Lymphoma derived (BL) and lymphoblastoid (normal lymphocyte) derived cell line (LCL). BL lines, which are derived from malignant cells in tumor biopsies, are monoclonal, usually aneuploid with a specific chromosomal translocation, bear a characteristic glycoprotein pattern, and are tumorigenic in nude mice. The LCL lines are derived from normal B cells, are polyclonal, have a normal diploid karyotype, a glycoprotein pattern similar to stimulated normal B cells, and do not grow when explanted subcutaneously into nude mice. LCLs, however, do grow in nude mice when inoculated intracerebrally, suggesting that immunological restriction is important in controlling outgrowth of EBV-carrying cells, even in a xenogeneic host. Reports of polyclonal outgrowths of karyotypically normal EBV-carrying cells in immunodeficient individuals confirm this observation (Houweling, A., P. J. van den Elsen, A. J. van der Eb [1980] *Virology* 105:537; Rassoulzadegan, M., A. Cowie, A. Carr, N. Glaichenhaus, R. Kamen, F. Cuzin [1982] *Nature* 300:713; Treisman, R., U. Novak, J. Favaloro, R. Kamen [1981] *Nature* 292:595; Giovanella, B., K. Nilsson, L. Zech, O. Yim, G. Klein, J. S. Stehlin [1979] *Int. J. Cancer* 24:103).

In general, tumor cells develop from normal cells by a multistage process. Two critical stages include (a) immortalization, i.e., the ability to divide perpetually without exogenously supplied mitogenic stimuli, and (b) acquisition of resistance to negative homeostatic signals that normally regulate growth. These stages may be associated with cytokines because regulation of proliferation and differentiation in most eukaryotic cells is accomplished by the interaction of specific cytokines with cell surface receptors. Receptor activation is followed by transmembrane signal transduction which leads to the generation of specific second messenger molecules. These receptor dependent events result in a defined series of cytoplasmic and/or nuclear changes leading to regulation of cellular activity.

Autonomous growth, as a result of transformation associated events, occurs in normal B cells transformed in vitro by EBV, and also in B cells derived from EBV positive and negative malignancies. EBV-transformed normal B lymphocytes divide continuously in culture without help from T cells or macrophages. Factor dependent autostimulatory growth for EBV-carrying B lymphocytes has now been reported by many groups. This secreted growth enhancing activity is specific for mature lymphoid cells. In addition, immortalized EBV-carrying B cells respond differently than normal B cells to certain cytokines, e.g., they proliferate in response to TGFβ and IL-6. After EBV infection, B lymphocytes have an altered morphological appearance, produce immunoglobulin, and become independent of exogenous differentiation factors and resistant to saturation conditions in cell culture.

How lymphoid cells communicate with each other to affect cell growth, differentiation, and functional activities has been a major focus of investigation. The immune response to foreign antigens is dependent on the interactions of several different cell types, including macrophages, T, and B lymphocytes. The first described soluble growth factor of lymphoid origin, T cell growth factor (IL-2), was found in supernatants of lectin stimulated peripheral blood lymphocytes. Since the discovery of IL-2, various studies have described many additional growth factors and have begun to delineate the mechanisms controlling lymphocyte proliferation.

For the B lymphocyte, our understanding of the regulation of growth and differentiation has increased in complexity in the past few years. A plethora of factors, including BCGF (12 and 60 kD), IFNγ, TNFα, lymphotoxin, TGFβ, IL-1α, IL-1β, IL-2, IL-4, IL-5, IL-6, IL-7, IL-10, IL-12, IL-15 and C3 fragments have been reported to modulate the growth of human and/or murine B lymphocytes in cell culture studies. These effects include growth augmentation (BCGF), differentiation (IL-6), and inhibition of proliferation (TGFβ). It appears that many of the T lymphocyte derived immunomodulatory molecules which direct B lymphocyte activities also regulate pleomorphic T cell functions. Some affect growth (IL-2), whereas others can also cause changes in cellular differentiation (IL-3). IL-2 functions as a direct growth factor for T lymphocytes, but other factors (IL-1) are described as comitogens or "helper" factors for cells stimulated by antigen or mitogen. IL-1, however, has recently been reported to function as a direct growth factor for one T cell sub-clone (Orencole, S. F., C. A. Dinarello [1989] *Cytokine* 1:14). For murine lymphocytes, two distinct CD4 expressing helper T cell subsets, Th1 and Th2, have been identified which differ in terms of factor response and production. Strictly similar subsets of distinct human T lymphocytes have not yet been described. Murine Th2 T cells secret IL-10, a 17 kD molecule which can inhibit Th1 cell activity. IL-10 has extensive homology with an uncharacterized EBV gene, BCRF1 (Baer, R., A. T. Bankier, M. D. Biggin, P. L. Deininger, P. J. Farrell, T. J. Gibson, G. Hatfull, G. S. Hudson, S. C. Satchwell, C. Sequin, P. S. Tuffnell, B. G. Barrell [1984] *Nature* 310:207).

Several growth factors have been proposed to have stimulatory activity for EBV transformed cells. These include BCGF (Ambrus, J. L., A. S. Fauci [1985] *J. Clin. Invest.* 75:732), IL-1 (Blazar, B. A., L. M. Sutton, M. Strome [1986] *Canc. Immunol.* 22:62), CD23 (Swendeman, S., D. A. Thorley-Lawson [1987] *EMBO J.* 6:1637), an unidentified lymphokine, called autocrine B Growth Factor, aBGF (Buck, J., U. Hammerling, M. K. Hoffmann, E. Levi, K. Welte [1987] *J. Immunol.* 138:2923), and, most recently, IL-6 (Muraguchi, A., H. Nishimoto, N. Kawamura, A. Hori, T. Kishimoto [1986] *J. Immunol.* 137:179). Thus far, none of these molecules has been shown to be universally present or absolutely required for growth of EBV positive lymphoblastoid cell lines. BCGFs of 25–30 kD and 60 kD, which are similar to T cell derived lymphokines, have been identified in supernatants from EBV-carrying cells. 60 kD BCGF has been purified to homogeneity and, although an activator of stimulated normal B cells, it is not produced by all EBV-carrying lines or even by all cells in individual secretor lines. BCGF production has also been reported for activated normal B lymphocytes (Muraguchi et al., supra).

Certain EBV-carrying cells have been reported to function as antigen presenting cells, contain IL-1 like activity in their supernatants, and express mRNA for IL-1. One laboratory reported the purification of a novel IL-1 from an EBV-carrying line (Bertoglio, J., J. Dosda, R. Stancou, E. Wollman, D. Fradelizi [1989] *J. Mol. Cell Immunol.* 4:139) but later revised their findings (Bertoglio, J., E. Wollman, A. Shaw, L. Rimsky, D. Fradelizi [1989] *Lympho. Research* 8:19). This same laboratory now reports that an IL-1-like activity (ADL) is elicited by a 12 kD protein produced by both EBV and HTLV-1 transformed cells (Wakasugi, H., N. Wakasugi, T. Trusz, Y. Tagaya, J. Yodoi [1989] *J. Immunol.* 142:2569; Tagaya, Y., Y. Maeda, A. Mitsui, N. Kondo, H. Matsui, J. Hamuro,, N. Brown, K. Arai, T. Yokota, H. Waksugi, J. Yodoi [1989] *EMBO J.* 8:757). Cloning of this protein, ADL, indicates it is a member of the human thioredoxin family with no direct relatedness to IL-1, although it may enhance IL-1 functions. Vigorous attempts by our laboratory using both Northern blotting and reverse transcription polymerase chain reaction (RT-PCR) demonstrate clearly that neither IL-1α nor IL-1β is expressed by these NAD-20 cells.

CD23, originally identified as a 45 kD differentiation antigen on EBV-infected cells, is expressed on all activated human B cells and macrophages. CD23 is identical to the low affinity Fc receptor for IgE ($Fc_eR11$/CD23) (Defrance, T., J. P. Aubry, F. Rousset, B. Vandervliet, J. Y. Bonnefoy, N. Arai, Y. Takebe, T. Yokota, F. Lee, K. Arai, J. deVries, J. Banchereau [1987] *J. Exp. Med.* 165:1459). A soluble 25 kD form of CD23 is shed into cell supernatants. At present, there is much interest in CD23 because the latent EBV genes, EBNA 2 and LMP, appear to induce its expression in B lymphocytes (Wang, F., C. D. Gregory, M. Rowe, A. B. Rickinson, D. Wang, M. Birkenbach, H. Kikutani, T. Kishimoto, E. Kieff [1987] *Proc. Natl. Acad. Sci. USA* 84:3452). Some reports have suggested that it is a receptor for the low molecular weight BCGF (Gordon, J., A. Webb, G. R. Guy, L. Walker, M. Rowe [1986] *Eur. J Immunol.* 16:1627), and a shed form has been reported to function as an autocrine growth factor (Swendeman et al., supra). Conflicting reports, however, have also appeared. Recombinant shed $Fc_eR11$/CD23 did not stimulate B cell proliferation, whereas it did bind IgE (Uchibayashi, N., H. Kikutani, E. L. Barsumian, R. Hauptmann, F.-J. Schneider, R. Schwendenwein, W. Sommergruber, W. Spevak, I. Maurer-Fogy, M. Suemura, T. Kishimoto [1989] *J. Immunol.* 142:3901). Highly purified shed CD23 from supernatants failed to stimulate B cell growth, and CD23 on the plasma membrane was not demonstrated as the receptor for the low molecular weight BCGF.

Acquisition of an autocrine growth cycle, whereby a cell both secretes and responds to endogenous growth stimulating factors, may be one means by which cancer cells achieve autonomy. Normal B lymphocytes transformed by EBV and malignant cell lines containing the EBV genome have been found to produce autostimulatory growth factors (Blazar, B. A., L. M. Sutton, M. Strome [1983] *Can. Res.* 43:4562).

BRIEF SUMMARY OF THE INVENTION

The subject invention concerns the discovery and purification of a novel secreted cytokine from Mycoplasma. This protein has been named IL-X. IL-X, which can be isolated by size exclusion HPLC on TSK-SW-3000 columns, migrates at an apparent molecular weight of approximately 42 kD in SDS-polyacrylamide gels. Thus, this protein is referred to herein as the 42 kD IL-X protein, but it should be recognized that, due to the nature of SDS-PAGE analysis, the molecular weight of the protein may deviate slightly from the 42 kD value. IL-X stimulates proliferation of both EBV-carrying B lymphocytes and CON A activated normal T lymphocytes, suggesting a diverse role in control of lymphocyte proliferation. Growth of EBV-carrying lymphoblastoid cells is significantly reduced by antibody directed against either native IL-X or IL-X derived peptides (p-IL-X).

IL-X, either alone or in combination with other immunoregulatory molecules, can contribute to the establishment of long term lines of normal B cells in vitro. Such lines can also be used to generate monospecific human antibodies.

Severe pathology resulting from the uncontrolled proliferation of EBV-transformed B cells occurs in neoplasia and fatal infectious mononucleosis, as well as in situations of immunosuppression, immunodeficiency, and AIDS. Antibodies that neutralize IL-X activity, antisense DNA, or other antagonists of IL-X can be used to inhibit IL-X bioactivity or IL-X receptor function. For example, antibodies or other antagonists can be used to interrupt autocrine loops established in B cell neoplasia. Alternatively, exogenous replacement of IL-X can ameliorate certain B cell or T cell immunodeficiencies.

The subject invention also concerns isolated polynucleotide molecules which encode IL-X proteins.

BRIEF DESCRIPTION OF THE SEQUENCES

Figure 1:
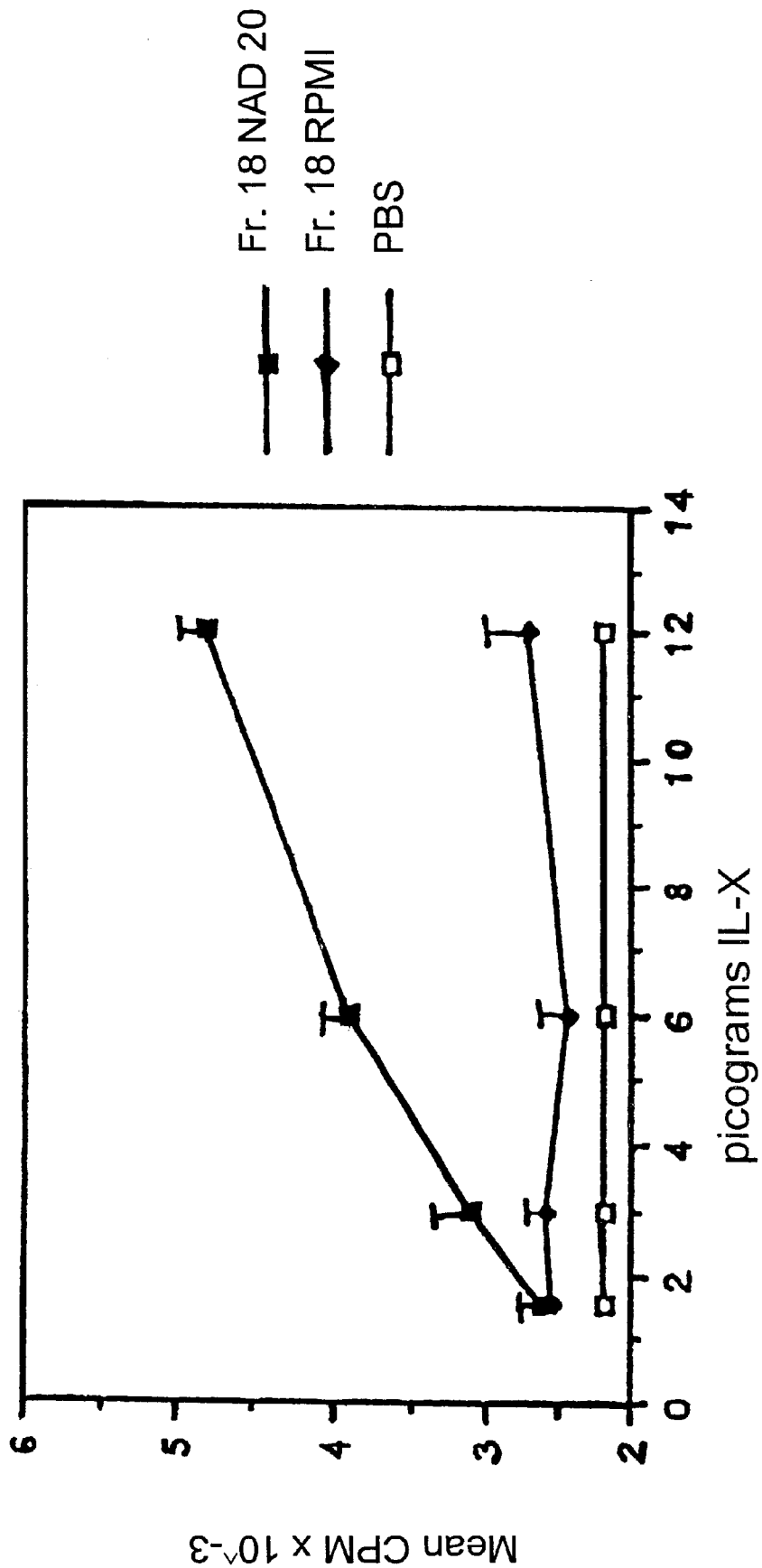
FIG. 1 shows the effect of size exclusion HPLC column fraction 18 (comprising IL-X) from the separation of NAD-20 medium and RPMI control medium on growth of NAD-20 cells ($10^3$/well) in $^3$H-thymidine assays. Estimate of picograms of IL-X is determined from silver stained SDS-PAGE gels with a sequentially diluted standard.

SEQ ID NO. 1 is tryptic fragment A from IL-X.

SEQ ID NO. 2 is tryptic fragment B from IL-X.

SEQ ID NO. 3 is tryptic fragment C from IL-X.

SEQ ID NO. 4 is a hypothetical 10-amino acid fragment corresponding to reported positions 2–11 of tryptic fragment A.

SEQ ID NO. 5 is a 48-mer oligonucleotide probe that can be used according to the subject invention.

SEQ ID NO. 6 is the RT-PCR fragment from IL-X.

SEQ ID NO. 7 is a DNA sequence obtained by a reverse transcriptase-polymerase chain reaction procedure.

SEQ ID NO. 8 is a DNA sequence of *Mycoplasma fermentans* encoding an IL-X polypeptide having an amino acid sequence shown in SEQ ID NO. 9.

SEQ ID NO. 9 is an amino acid sequence of an IL-X polypeptide encoded by the DNA sequence shown in SEQ ID NO. 8.

SEQ ID NO. 10 is the complete amino acid sequence for tryptic fragment A from IL-X.

SEQ ID NO. 11 is the complete amino acid sequence for tryptic fragment C from IL-X.

SEQ ID NO. 12 is a consensus sequence for prokaryotic signal peptidase II.

SEQ ID NO. 13 is a DNA sequence of *Mycoplasma fermentans* encoding an IL-X polypeptide having an amino acid sequence shown in SEQ ID NO. 16.

SEQ ID NO. 14 is an amino acid sequence of an IL-X polypeptide encoded by the DNA sequence shown in SEQ ID NO. 8.

SEQ ID NO. 15 is an amino acid sequence of an IL-X polypeptide encoded by the DNA sequence shown in SEQ ID NO. 13.

SEQ ID NO. 16 is an amino acid sequence of an IL-X polypeptide encoded by the DNA sequence shown in SEQ ID NO. 13.

DETAILED DISCLOSURE OF THE INVENTION

The present invention concerns novel prokaryotic-derived cytokines (also known as prokines). The prokine of the invention, a protein referred to herein as IL-X, has an apparent molecular weight of about 42 kD and can be isolated from Mycoplasma. Analysis of the amino acid sequence of three peptides obtained by tryptic digest of IL-X indicates that this molecule has not been previously described. The IL-X protein of the subject invention augments proliferation of both B and T lymphocytes, suggesting broad immunoregulatory effects for this protein. In addition, the growth of EBV-transformed human B lymphocyte lines is reduced by either antibody to IL-X protein or antibody to an IL-X peptide. As described herein, peptide sequences can be used to construct oligonucleotides to screen cDNA libraries for IL-X cDNA and to generate antibodies that bind to IL-X. Recombinant protein can be used for functional studies, receptor isolation and for the preparation of monospecific antisera.

In one embodiment, an IL-X protein comprises the amino acid sequence shown in SEQ ID. NO. 9. Another embodiment of the protein of the subject invention comprises the amino acid sequence of the protein shown in SEQ ID NO. 14 wherein the first twenty-four (24) amino acid residues of the protein shown in SEQ ID NO. 9 have been deleted.

The IL-X proteins of the subject invention have a variety of uses. For example, IL-X, or fragments or derivatives thereof, can be used to raise antibodies as described herein. Also, IL-X, or fragments or derivatives thereof, can be used to enhance the growth of cells in vitro. In one preferred embodiment of the subject invention, an IL-X protein can be used to grow primary human B cell cultures. This has not previously been possible in any consistent way. The capacity to grow normal B cell cultures will facilitate investigation of B cell biology and growth regulation in non-transformed cells. Thus, an IL-X protein can be added to primary human B cell cultures to facilitate proliferation of these cell lines. Such cell lines can also be used advantageously in the production of human monoclonal antibodies.

The IL-X proteins can also be used in therapeutic or prophylactic situations. Such situations would include, for example, disease states associated with diminished levels of IL-X. For example, IL-X may be administered to enhance B cell or T cell proliferation to alleviate conditions associated with diminished B cell or T cell populations.

As would be readily appreciated by one skilled in this art, the IL-X proteins of the subject invention can also be used as molecular weight standards, or as inert proteins in an assay. The polypeptides can also be used to detect the presence of antibodies that are immunoreactive with IL-X.

A further utility of the subject invention concerns the development of immunological reagents to recombinant IL-X (rIL-X) for diagnosis and treatment. Antibodies raised to an IL-X protein can have a variety of uses. For example, such antibodies may be used for purification or identification of IL-X. Also, such antibodies may be useful in therapeutic or prophylactic applications where it is desired to inhibit the activity of IL-X. Such situations would include, for example, disease states associated with increased levels of IL-X or associated with excessive B or T cell proliferation, including those disease states mediated by the Epstein-Barr virus. This could include neoplasia, B cell lymphomas, and cases of severe mononucleosis.

IL-X activity may also be inhibited by the administration of soluble IL-X receptors that would bind with IL-X and inhibit its normal biological activity. Alternatively, analogs of IL-X could be designed that would bind to IL-X receptors without activating those receptors. In yet another example, antibodies to the receptors could be administered. Such antibodies could sterically block the receptors, thereby preventing binding by IL-X. Other methodologies and variations of these methodologies would be apparent to one skilled in the art.

The administration of IL-X proteins or antibodies to IL-X would be in accordance with standard techniques and formulations useful for administering such proteins and antibodies. In one embodiment, the IL-X proteins or anti-IL-X antibodies may be conjugated to antibodies or receptors. These antibodies or receptors could then direct the IL-X biological activity to a desired location in the body.

As used herein, reference to IL-X protein refers to the approximately 42 kD protein (as measured by SDS-PAGE) specifically exemplified herein, as well as fragments, precursors, analogs, or derivatives of that 42 kD protein that retain biological or immunological characteristics associated with the 42 kD protein. As described herein, a deduced amino acid sequence of an IL-X protein (lacking a presumed signal peptide sequence) has an apparent molecular weight of about 45 kD.

A further aspect of the invention pertains to polynucleotide sequences which encode IL-X proteins. In one embodiment, a polynucleotide of the subject invention comprises the nucleotide sequence shown in SEQ ID NO. 8. SEQ ID NO. 8 shows a nucleotide sequence isolated from a *Mycoplasma fermentans* genomic clone containing an IL-X open reading frame. SEQ ID NO. 8 also shows the deduced amino acid sequence of the polypeptide encoded in the reading frame. The reading frame encodes a 428 amino acid precursor polypeptide (SEQ ID NO. 9) with a predicted molecular weight of 47.7 kD. In one embodiment of the invention, this protein is likely cleaved at the seven amino acid consensus sequence (VAVSCGN) (SEQ ID NO. 12) for prokaryotic signal peptidase II between the serine 24 and cysteine 25 to yield a mature protein of 45.3 Kd having the amino acid sequence shown in SEQ ID NO. 14. Preferably, the polynucleotide comprises at least the nucleotide sequence from nucleotide 198 through nucleotide 1481 of the nucleotide sequence shown in SEQ ID NO. 8. In another embodiment, a polynucleotide of the subject invention comprises nucleotide 270 through nucleotide 1481 of the nucleotide sequence shown in SEQ ID NO. 8. Also contemplated within the scope of the present invention are fragments and variants of the polynucleotide encoding IL-X. For example, in one embodiment, the nucleotide at position 612 of the SEQ ID NO. 8 sequence is changed from a "C" to a "T". This change results in the substitution of the histidine coded for at that position to a tyrosine residue at that position.

The polynucleotide sequences of the subject invention may be composed of either RNA or DNA. Preferably, the polynucleotide sequences are composed of DNA. A full length gene encoding the all or part of the IL-X protein and any precursor can be obtained as described herein. Also, a person skilled in the art could readily synthesize DNA sequences encoding IL-X protein or peptides. Specific examples of an IL-X protein and peptides are provided herein. The nucleotide sequences encoding the peptides could be used to produce recombinant peptides, or they could be used as probes or as primers for diagnostic and/or analytical PCR procedures. The polynucleotides of the subject invention can also be used as DNA or RNA sizing standards. Methods for obtaining full length genes are described in greater detail below.

The subject invention also concerns IL-X encoding polynucleotides incorporated into cloning and expression vectors. Host cells, either eukaryotic or prokaryotic, comprising the IL-X polynucleotides or vectors containing IL-X polynucleotides, are also contemplated within the scope of the invention.

The subject invention also concerns polynucleotides that are antisense to polynucleotide sequences encoding an IL-X protein. The activity of IL-X can be inhibited by the administration of antisense DNA that would specifically bind to the DNA that encodes IL-X. Such an administration of antisense DNA would block the production of IL-X, thereby reducing or eliminating its biological activity. The antisense DNA can be administered by techniques known in the art, including encapsulation in liposomes.

The present invention also concerns receptors that bind the subject IL-X proteins. These subject IL-X receptors can be isolated from cells that bind IL-X, such as NAD-20 cells, according to the teachings of the subject invention.

As used herein, the term "isolated" refers to obtaining a protein or antibody in a form other than that which occurs in nature. This may be, for example, obtaining IL-X by purifying crude samples, or it could be the recovery of recombinant IL-X from transformed cell lines. In the case of polynucleotide sequences, "isolated" would mean, for example, that the sequence is no longer associated with other DNA sequences with which it would naturally occur. Thus, the claimed polynucleotide sequence may be placed into a plasmid or other vector or transformed or transfected into the genome of a host. In the case of antibodies, "isolated" refers to antibodies which, through the hand of man, have been produced or removed from their natural setting. Thus, isolated antibodies according to the subject invention would include antibodies raised as the result of purposeful administration of IL-X compounds to an appropriate host.

Materials and Methods

IL-X Biomass. Cultures of NAD-20 LCL demonstrated to be free of mycoplasma contamination by PCR are plated in RPMI medium at $10^4$ cells/well in flat-bottom 96-well microtitre plates. The bioactivity and dose response of each of the IL-X proteins can be evaluated by the addition of the rIL-X protein at concentrations over several orders of magnitude in the pg-ng/ml range. The proliferation of NAD-20 cells in triplicate wells are determined after three days of incubation using the $^3$H-thymidine incorporation assay as previously described by Blazar et al. (1990), or by use of the more convenient, non-radioactive MTT assay (Klotz, E. L. [1990] *Department of Biological Sciences, Wellesley College Honors Thesis*).

Isolation of DNA encoding IL-X. Polynucleotide encoding an IL-X protein was isolated from mycoplasma. Identification of the species of mycoplasma as *Mycoplasma fermentans* was accomplished by PCR using the ATCC detection kit (#90-1001K). To isolate the gene, *Mycoplasma fermentans* genomic DNA was purified, and both EcoRI and HaeIII digested genomic libraries were prepared in the lambda ZAP II vector (Stratagene, LaJolla, Calif.) using standard procedures. These libraries were then screened with various IL-X cDNA or PCR oligonucleotide probes described herein. Clones from both libraries were isolated that contain the complete IL-X gene and various lengths of flanking genomic sequence including the promoter. These mycoplasma genomic inserts were excised in vivo using the Stratagene helper phage system as pBLUESCRIPT phagemids. One clone contained a 1284 bp open reading frame (ORF)(encoding a polypeptide of 428 amino acids including the 166 residues containing the three tryptic peptides A, B and C (SEQ ID NOS. 1, 2 and 3) derived from the 42 kD protein partially purified from concentrated NAD-20 culture medium. The predicted amino acid sequence of IL-X yields a protein with a molecular weight of 47.7 kD, suggesting that IL-X is perhaps synthesized as a high molecular weight precursor (pro-IL-X) that can be proteolytically processed to a "mature" 42 kD molecule found in NAD-20 conditioned medium. SEQ ID NO. 8 shows the nucleotide sequence of a polynucleotide molecule that encodes an IL-X protein. The deduced amino acid sequence is also shown.

One of the characteristic features of mycoplasma genes is the use of an alternate genetic code, where the "universal" stop codon TGA encodes the amino acid tryptophan. Therefore, to achieve expression of IL-X in any other system using the universal code, these TGA codons must be mutated to TGG. In addition, for expression in non-mycoplasma prokaryotes such as *E.coli*, codons may need to be modified to those codons favored for that particular expression system.

Expression of recombinant and further purification of IL-X protein. IL-X protein encoded by full-length genomic clones isolated from the phage library and having modified codons to correct for codon usage in non-mycoplasma expression systems as discussed above can be expressed in *E. coli*. For example, IL-X can be expressed as a β-galactosidase fusion protein following IPTG induction. Antibodies to IL-X protein can be used to screen the library for an in-frame clone by standard procedures. Bacterial cell lysates can be used to raise crude polyclonal antibodies in rabbits and rats and adsorbed against lysaies from non-recombinant *E. coli* host cells yielding antisera relatively specific for IL-X. This antibody can serve as a preliminary reagent in Western blot analysis of IL-X until highly purified protein can be obtained to use in the production of monoclonal and mono-specific polyclonal antibodies. This antibody therefore enables one to determine whether IL-X is expressed exclusively in cells of the B lineage. Additionally, by use of crude lysates in growth assays with EBV-ECL, one can determine whether the cDNA clones selected encode an active factor.

One IL-X genomic clone containing the entire ORF was used as a PCR template for primers designed with vector-specific 5' extensions to facilitate subcloning into the *E. coli* expression plasmid pET-32 (Novagen) using ligation-independent cloning (LIC). The sense primer also incorporates a cleavage recognition sequence for the protease Factor Xa to allow removal of vector encoded detection/purification tags (i.e., thioredoxin, S-Tag, and His-Tag) that are attached to the amino terminal end of the fusion protein, thus providing recombinant IL-X protein containing only native sequence. Initially, it was decided to try expressing pro-IL-X in a soluble form and, therefore, the pET32 vector was selected. This version of the pET expression plasmid carries the thioredoxin protein as part of the vector-encoded sequences. It has been found that expressing inherently insoluble proteins in E.coli fused to thioredoxin substantially increases their solubility (Novy, R., J. Berg, K. Yaeger, R. Mierendorf [1995] inNovations 3: 7–9).

In addition to the amplification of the full-length reading frame for pro-IL-X, two subfragments were also prepared. Primers were designed to include a TAA stop codon 186 amino acid residues into IL-X to allow expression of a N-terminal peptide. A second C-terminal peptide was designed using an upstream primer to incorporate an ATG initiator methionine before amino acid 187 in "native" IL-X. This C-terminal clone represents that portion of IL-X containing the three tryptic peptides A, B and C (SEQ ID NOS. 1, 2 and 3). To minimize PCR-induced mutations, all amplicons for subcloning were synthesized using the thermostable DNA polymerase Deep Vent (New England Biolabs) which possesses proof-reading activity. The pET-32/IL-X recombinant plasmids were sequenced to verify fidelity before transmission into the E.coli expression host strain BL21 (DE3).

Once the fidelity of an IL-X clone is established, then large-scale expression of recombinant protein can be undertaken using, for example, a baculovirus expression system. An IL-X cDNA insert can be sub-cloned into a modified form of the original Summers (Lukow, V. A., M. D. Summers [1989] Virology 170:31) baculovirus transfer vector pVL1392. The modification to this vector system is the addition of six tandem histidine residues either at the amino or carboxyl-terminus of the expressed protein to facilitate one-step purification by binding to immobilized $Ni^{2+}$ affinity columns (Qiagen, InVitrogen Corp.). The recombinant IL-X isolated in this fashion can be used directly for antibody production. If desired, the histidine sequence can be removed by enzymatic cleavage using a rare protease-sensitive site situated at the junction of the histidine tag and the N-terminus of the encoded protein. Throughout the purification scheme, the location of functional recombinant IL-X can be evaluated both by addition to growth assays with EBV-LCL and by Western blot analysis after SDS-PAGE of extracts and column fractions.

Radiolabelling of IL-X

Recombinant IL-X radiolabelled for receptor binding assays can be produced as described herein. It has been previously demonstrated that replacement of the native 5' untranslated sequence in eukaryotic mRNAs with a plant viral leader significantly enhances their cell-free translation (Jobling, S., L. Gehrke [1987] Nature 325: 622–625). The 37 bp untranslated leader (UTR) of alfalfa mosaic virus can be incorporated between the ribosome binding site and the initiator methionine of the thioredoxin Tag of the pET32 vector by PCR. The effect of this enhancer on the level of rIL-X translation can be assessed in the Novagen single tube transcription-translation system (STP3) containing 35S-methionine (Mierendorf, R., M. McCormick [1998] inNovations 8: 1–5). A similar translational enhancer element from the Xenopus β-globin 5'-UTR has already been incorporated into other Novagen vectors (e.g., pT7Blue-2). In addition, rapid in vitro labelling with either $^{32}P$ or $^{33}P$ to >$10^5$ cpm/μg in a protein kinase A (PKA) driven phosphorylation reaction can also be achieved for purified proteins expressed in yet another new Novagen vector (pET33), since the fusion proteins carry the five (5) amino acid recognition sequence for the catalytic subunit of PKA (Blanar, M. A., W. J. Rutter [1992] Science 256: 1014–1018). Subcloning of the various IL-X sequences into these vectors provides alternative ways to isolate labelled protein for receptor binding studies. Proteins labelled by any of these methods can again be purified using His-Tag affinity matrix cartridges. All rIL-X proteins isolated in this way can be desalted, concentrated and transferred to PBS by dialysis or ultrafiltration prior to storage, gel analysis or use in further experiments. Using the IL-X construct of the subject invention, high specific activity IL-X can be produced in vitro.

Figure 3:
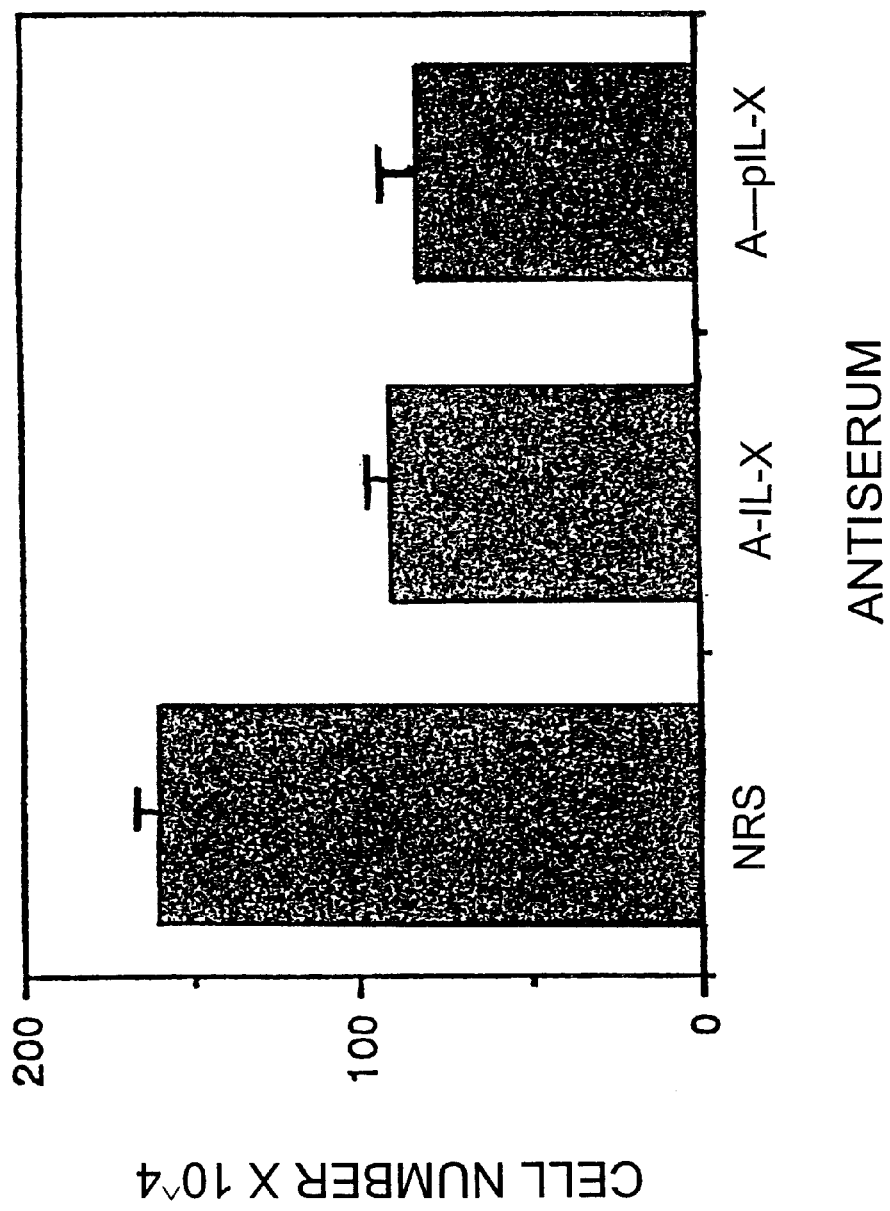
FIG. 3 shows mean growth of NAD-20 cells enumerated in triplicate cultures on day 4 following the addition of 5% rabbit serum. Differences in growth between the NRS (normal prebleed) serum and the anti pIL-X serum and between the NRS and the anti IL-X serum are significant ($p<0.05$).

Production of monospecific antibodies. As described herein, two rabbit antisera have been raised to IL-X. One serum was produced by immunizing with IL-X protein obtained from SDS-PAGE gels; the second serum was produced using a KLH coupled 18 amino acid peptide (pIL-X) synthesized to correspond with an internal amino acid sequence from IL-X. Both antisera react with native IL-X on dot blots. In experiments with NAD-20 cells, these same sera interfered with cell growth (FIG. 3). Both of these antibodies can be used for the examples outlined below.

Additional antibodies to IL-X can be made using, for example, the following immunogens:

(i) The IL-X peptide (pIL-X) which is recognized on the native IL-X protein by rabbit anti-pIL-X; this antiserum can be made in rats and enables the development of a specific ELISA for IL-X. Alternatively, the presently available rabbit anti-IL-X could be biotinylated and used directly for ELISA development.

(ii) Synthesized peptides prepared from the other sequenced tryptic fragments of IL-X; this antiserum can be made in rabbits or other animals.

(iii) Recombinant IL-X; this antiserum can be made in rabbits or other animals and can provide a more specific reagent for the entire IL-X molecule than the antiserum raised against IL-X from SDS-PAGE gels.

Positive heterosera can be affinity purified by column chromatography with the synthesized peptide or on a microscale using nitrocellulose strips containing IL-X. Identity of IL-X material can be established by ELISA, immunoprecipitation, and/or immunoblot by standard techniques. Antisera produced can be evaluated for specificity with appropriate cell and lysate controls and can be tested for reactivity against other known cytokines.

Monoclonal antibodies can be produced against IL-X to obtain even greater specificity, although the raising of monoclonal antibodies is not essential to these experiments. ELISAs, used to screen hybridomas for antibody production, can be performed also with recombinant or HPLC-purified IL-X. Antibody to mouse IgG coupled to alkaline phosphatase can be used as a probe. In addition, monoclonal antibodies can be raised by standard techniques to small peptides synthesized to correspond to amino acid sequences obtained from tryptic fragments of IL-X such as pIL-X.

Following are examples which illustrate procedures, including the best mode, for practicing the invention. These examples should not be construed as limiting. All percentages are by weight and all solvent mixture proportions are by volume unless otherwise noted.

EXAMPLE 1

Biochemical Purification of IL-X

IL-X can be purified from supernatants of cell lines infected with *Mycoplasma fermentans* or from supernatants of *M. fermentans* cultured in the absence of eukaryotic cells. IL-X can be purified from these supernatants by size exclusion HPLC on TSK-3000 gel filtration columns. In addition, a polynucleotide molecule comprising a nucleotide sequence encoding an IL-X polypeptide will be deposited with the American Type Culture Collection (ATCC), 12301 Parklawn Drive, Rockville, Md. 20852 USA.

Concentrated supernatants were prepared from the *M. fermentans*-infected NAD-20 cell line by a 24 hour incubation of logarithmically growing cells in RPMI, followed by passage through an Amicon stir cell containing a Spectrapore ultra filter with a 1000 MWCO pore size. Following dialysis, concentrated supernatant applied to the column was eluted with phosphate buffered saline (PBS) and monitored at an absorbance of 280 nm. Four-milliliter fractions were collected and tested for activity. The B lymphocyte growth stimulatory activity was recovered in fractions 18–20 with an occasional trailing peak at fraction 22. Column fractions were concentrated 10 times and processed on SDS-PAGE gels. Only one band, with an apparent molecular weight of 42 kD, was detectable by silver stain. The molecular weight appeared to be identical in size when electrophoresis was performed under both reducing and nonreducing conditions.

Purification of IL-X by HPLC results in a substantial removal of this protein from concentrated supernatants. Approximately 40% of the growth stimulatory activity in unfractionated supernatants is recovered in the active HPLC fractions. In Table 1, data are presented for one purification of IL-X. Values for specific activity may be inaccurate, as silver stain is imprecise for this purpose.

TABLE 1

Purification of IL-X

| Source | Protein content*** ng/μl | Stimulatory activity Experimental** | Stimulatory activity CPM/μl | Specific activity (activ/ng) | Units/mg* |
|---|---|---|---|---|---|
| NAD-20 medium | 0.04 | 1429/100 μl | 14.29 | 357.3 | |
| HPLC Frac-18 NAD-20 | 0.002 | 917/12.5 μl | 73.46 | 36,680.0 | $3.7 \times 10^8$ |

***estimate based on silver stained SDS-PAGE gel
**average CPM over control
*1 unit is defined as causing a 100% increase in $^3$H-thymidine uptake Although the apparent molecular weight of IL-X, 42 kD, indicates that IL-X is larger than most immunomodulatory molecules, we have in addition demonstrated by functional assay and mRNA analysis that IL-X is not IL-1α or IL-1β (mRNA), IL-2 (CTLL2 cells), IL-3 (DA1 cells), IL-4 (monocyte CD23 induction), IL-5 (Western blot using antibody from Genetics Institute), TNFα (ELISA, Cistron Biotechology, Inc.), or IL-6 (B9 cells).

EXAMPLE 2

Molecular Characterization of IL-X

IL-X was purified from concentrated supernatants by SDS-PAGE and electrophoretically transferred onto nitrocellulose. The nitrocellulose was stained with Ponceau S and the appropriate band was excised. This band on the nitrocellulose was incubated with PVP-40 and digested with trypsin. At this stage tryptic fragments could be resolved by reverse-phase HPLC. The IL-X used for purification was obtained from an SDS-PAGE gel and selected by molecular weight. As IL-X is the same apparent molecular weight as actin, the most abundant protein in cells, we felt it was necessary to first select tryptic fragments for sequencing which could not contain any possible actin contaminants. Concentrated IL-X containing medium and purified actin were individually separated by SDS-PAGE, transferred to nitrocellulose, and digested with trypsin in parallel. The tryptic fragments from IL-X and actin were processed by reverse phase HPLC in an identical manner. A comparison of the peptide maps indicates that there are several tryptic fragments unique to IL-X that are not similar to any tryptic fragments found in actin. Tryptic fragments unique to IL-X were sequenced. Three HPLC fractions containing well-separated fragments were transferred to PVDF membrane and sequenced in a gas phase sequenator.

Amino acid sequence of 3 tryptic fragments from IL-X. The following sequences were determined:

Tryptic Fragment A

[SER], ILE, GLY, VAL, ALA, GLU, ASN, —, PHE, (GLY), ASN (SEQ ID NO. 1)

Tryptic Fragment B

TYR, ASN, PRO, HIS, VAL, ILE, LEU, SER, VAL, ALA, GLY, PRO, ALA, THR, PHE, GLU, THR (SEQ ID NO. 2)

Tryptic Fragment C

VAL, VAL, ALA, SER, PHE, GLY, GLY, GLY, ALA, PHE, PRO, GLY, VAL, THR, THR, PHE, ASN, GLU, GLY, PHE, (ASN), (GLY) (SEQ ID NO. 3)

Because of the ambiguity of positions 1, 8, and 10 of tryptic fragment A, the following hypothetical 10 amino acid sequence generally corresponding to positions 2–11 of fragment A was used for comparison with reported molecules to overcome any ambiguity:

ILE, GLY, VAL, ALA, GLU, ASN, any aa, PHE, any aa, ASN (SEQ ID NO. 4)

The sequences for tryptic fragments B and C were used for comparison purposes. A search in the most recent National Biomedical Research Foundation Protein Library, most recent GenBank Translated version, and the Swissprotein databank, the National Center for Biotechnology Information (NCBI) Peptide Sequence database, and the latest Entrez release (6.0) using the BLAST Internet services, found neither identity nor similarity for tryptic fragments A, B, or C with any reported sequences.

Based on the deduced amino acid sequence (shown in SEQ ID NO. 8) from the genomic clone, the ambiguous or missing amino acid residues shown in tryptic peptides A, B and C have been identified or confirmed. Thus the complete amino acid sequences for each peptide is shown below:

Tryptic Fragment A

TRP, ILE, GLY, VAL, ALA, GLU, ASN, HIS, PHE, SER, ASN (SEQ ID NO: 10)

Tryptic Fragment C

VAL, VAL, ALA, SER, PHE, GLY, GLY, GLY, ALA, PHE, PRO, GLY, VAL, THR, THR, PHE, ASN, GLU, GLY, PHE, ALA, LYS (SEQ ID NO: 11)

The amino acid sequence of an IL-X peptide fragment derived from a reverse-transcriptase-polymerase chain reaction (RT-PCR) product was also determined. The RT-PCR product has the DNA sequence shown in SEQ ID NO. 7. The RT-PCR product was obtained using synthetic degenerate oligonucleotide primers based on tryptic peptide sequences A, B, and C.

A 48-mer sense-strand oligonucleotide (termed C+) was made based upon the amino acid sequence of tryptic peptide C using the neutral base inosine at positions of 4-fold, third position degeneracy in the genetic code. Two anti-sense, 64-fold degenerate 18-mers (A− and B−) were also synthesized based upon the amino acid sequences of the IL-X tryptic fragments A and B, respectively. These anti-sense oligonucleotides were each used to prime NAD-20 cellular RNA in a reverse transcriptase driven first strand cDNA reaction, followed by PCR amplification using the sense strand C+ 48-mer. RT-PCR of NAD-20 RNA using primers C+ and A– yielded an ≈480 bp fragment (CA), whereas a combination of primers C+ and B– on the same template generated a product CB of ≈220 bp in length. The 220 bp CB fragment could also be re-amplified using the CA fragment as the template primed with the oligonucleotides B– and C+, whereas oligonucleotides A– and B– produced no PCR product in the same reaction. Based upon these PCR reactions, we inferred the order and spacing of peptides in IL-X to be C, B, A. Complete sequencing of the CA fragment after direct subcloning into the T/A plasmid pCRII (InVitrogen Corp.) yielded a 498 bp nucleotide sequence that encodes all three tryptic peptides (C, B, and A) in frame within a 166 amino acid portion of the IL-X protein.

IL-X RT-PCR Fragment

Phe Gly Gly Gly Ala Phe Pro Gly Val Thr Thr Phe Asn Glu Gly Phe Ala Lys Gly Ile Leu Tyr Tyr Asn Gln Lys His Lys Ser Ser Lys Ile Tyr His Thr Ser Pro Val Lys Leu Asp Ser Gly Phe Thr Ala Gly Glu Lys Met Asn Thr Val Ile Asn Asn Val Leu Ser Ser Thr Pro Ala Asp Val Lys Tyr Asn Pro His Val Ile Leu Ser Val Ala Gly Pro Ala Thr Phe Glu Thr Val Arg Leu Ala Asn Lys Gly Gln Tyr Val Ile Gly Val Asp Ser Asp Gln Gly Met Ile Gln Asp Lys Asp Arg Ile Leu Thr Ser Val Leu Lys His Ile Lys Gln Ala Val Tyr Glu Thr Leu Leu Asp Leu Ile Leu Glu Lys Glu Glu Gly Tyr Lys Pro Tyr Val Val Lys Asp Lys Lys Ala Asp Lys Lys Trp Ser His Phe Gly Thr Gln Lys Glu Lys Trp Ile Gly Val Ala Glu Asn (SEQ ID NO: 6)

The amino acid sequences corresponding to tryptic peptides C, B, and A are shown in bold letters, above, and are located within the RT-PCR peptide fragment. The sequence is given beginning at the amino terminal end of the peptide fragment. The RT-PCR peptide fragment shows no significant matches or degree of homology to any proteins or polypeptides currently contained in any NCBI database. Furthermore, the RT-PCR cDNA fragment also lacks homology with any nucleotide sequence in the NCBI and Entrez nucleotide sequence database. Accordingly, the above amino acid sequences are concluded to be unique, and belong to a novel approximately 42 kD protein designated IL-X.

EXAMPLE 3

Purified IL-X Enhances B Cell Growth

The column fractions containing detectable IL-X enhance growth of NAD-20 cells as determined by $^3$H-thymidine incorporation. NAD-20 cells were incubated at low density to arrest their growth rate before use in these assays. Results of one representative experiment with HPLC fraction 18 are presented in FIG. 1. HPLC column fraction 18, which contained the greatest amount of material on SDS-PAGE, also exhibited the greatest amount of activity in B lymphocyte growth assays compared to HPLC fractions.

Studies with rabbit antibody to rIL-1α and rabbit antibody to rIL-1β demonstrated that these antibodies did not significantly reduce the enhancement of B cell growth by IL-X.

EXAMPLE 4

Further Characterization of Biological Activity of IL-X

Figure 2:
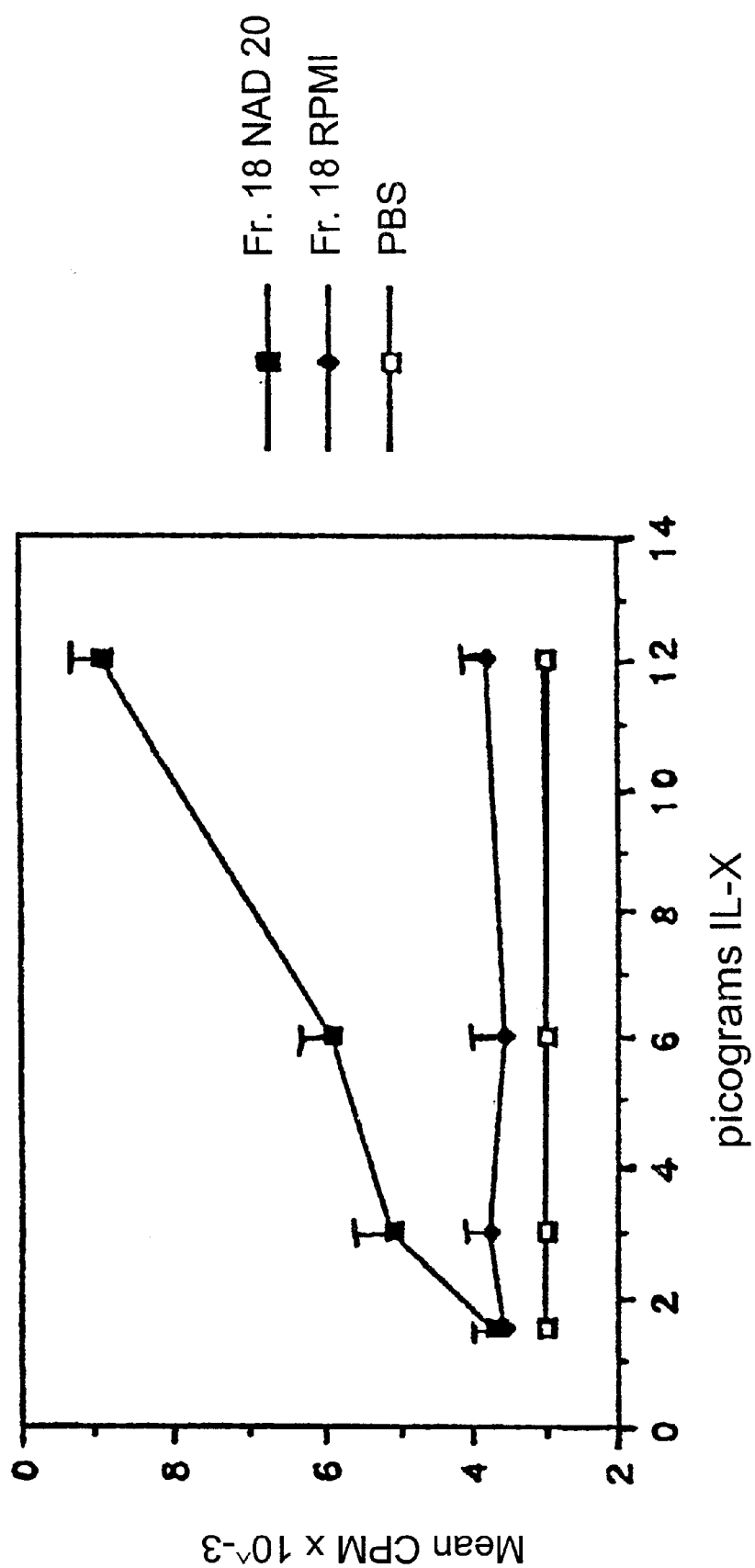
FIG. 2 shows effect of HPLC column fractions from NAD-20 medium and RPMI control on CON A-stimulated D10.G4.1 cells ($10^4$/well). Estimate of picograms IL-X is determined by silver stained SDS-PAGE gels with sequentially diluted standard.

Unfractionated supernatants from EBV-carrying lymphoblastoid cell lines contain growth stimulatory activity for human T lymphocytes. These supernatants enhance proliferation of CON A activated human T lymphocytes. They also are active in assays with PHA activated murine thymocytes. These same supernatants do not contain IL-2 as indicated by their inability to support growth of CTLL 2 cells. The HPLC column fractions which contained detectable IL-X costimulated the proliferation of the CON A murine T cell clone, D10.G4.1. D10.G4.1 is an IL-2 dependent helper T cell which is commonly used to assay for the comitogenic effect of IL-1. Results of one representative experiment with HPLC fraction 18 are presented in FIG. 2. As in the case of IL-1, human IL-X appears to enhance lymphoid cell growth without species restriction.

EXAMPLE 5

Demonstration that IL-X Does Not Enhance the Growth of an Epithelial Cell Line

Neither the unfractionated IL-X containing supernatant nor HPLC fraction 18 enhanced growth of H-135, a colon carcinoma cell line. This suggests that IL-X may exhibit some specificity as a regulatory molecule.

EXAMPLE 6

Development of Antibodies to IL-X (1) Antibodies to entire IL-X molecule. IL-X, separated by SDS-PAGE from concentrated (4000×) NAD-20 supernatants, was cut out of gels. Gel slices were ground, emulsified in Freund's adjuvant, and injected subcutaneously into a rabbit. Following subsequent immunizations, rabbit antiserum to IL-X (anti-IL-X) was prepared by standard techniques. Rabbit anti-IL-X recognizes the native IL-X protein on dot blots and SDS-PAGE processed IL-X protein on Western blots.

(2) Antibodies to IL-X peptide. An 18-amino acid peptide corresponding with the first 18 residues of the sequence for tryptic fragment C reported above was synthesized. This peptide was conjugated with KLH via cysteine and used to immunize a rabbit. This rabbit antiserum (anti-pIL-X) recognized the unconjugated peptide and the native IL-X protein on dot blots. The anti-pIL-X serum, however, does not recognize processed IL-X following SDS-PAGE and Western blotting techniques. Western blots probed with either enzyme or $^{125}$I conjugated goat anti-rabbit IgG were equally unsuccessful in demonstrating any binding of the anti-pIL-X antibody to IL-X.

As is known in the art, the techniques of SDS-PAGE and Western blotting cause antigen denaturation, and only denaturation-resistant epitopes on molecules can be recognized by antibodies. The inability to recognize epitopes destroyed by denaturing reagents is commonly experienced with monoclonal antibodies which bind with only one epitope. The epitope(s) on IL-X recognized by the anti-pIL-X serum has as its greatest possible dimension 18 residues of primary amino acid sequence and is likely to be considerably smaller due to possible intramolecular secondary and tertiary structure. In these Western blots, our rabbit anti-pIL-X functions more like a monoclonal than a polyclonal serum.

EXAMPLE 7

Demonstration that Antibody to IL-X Reduces B Cell Growth

In order to further evaluate the proliferative effect of IL-X on B lymphocytes, the rabbit antibodies to IL-X described above were added to growing B lymphocyte cultures. Growth of NAD-20 cells was significantly reduced, compared to growth in the presence of normal prebleed rabbit serum, by the addition of either rabbit anti-IL-X or by rabbit anti-pIL-X. Results from one preliminary experiment illustrating the mean number of cells after the addition of either control, anti-IL-X, or anti-pIL-X serum are presented in FIG. 3. The reduction of cell growth by specific antisera to IL-X provides additional proof of a role for IL-X in the growth of EBV-carrying B lymphocytes.

EXAMPLE 8
IL-X Receptor Cloning and Analysis rIL-X protein can be used to characterize and clone membrane-bound receptor on the LCL NAD-20 (and other cells if detected). The working model is that since IL-X is derived from a cellular parasite, it functions through a preexisting B cell receptor in a fashion demonstrated for other systems such as HIV, where chemokine receptors are utilized by the virus in this case to facilitate or aid infection (D'Souza, M. P., V. A. Harden [1996] *Nature Medicine* 2: 1293–1300). The specific activity of any radiolabelled IL-X should be compared to that of unlabeled in the NAD-20 bioassay to determine the reduction (if any) in activity caused by radiolabelling the molecule.

Molecular Cloning of IL-XR

Two major strategies to obtaining an IL-X receptor (IL-XR) cDNA are described below. One, expression cloning: a conventional, albeit labor-intensive approach which has been well-proven in the cytokine receptor field over the years; and two, phage-display: a somewhat less tried methodology especially for intact, large proteins, but one that has the potential to be far more rapid and less costly.

(a) Expression Cloning

An NAD-20 cDNA library directionally cloned into the Lambda ZAP Express vector system from Stratagene using a combination of oligo(dT) and random primed poly(A) enriched RNA has been prepared. This library has a cDNA insert size of >400 bp and a complexity of $6.4 \times 10^6$ primary plaques. The cDNAs can be excised from the lambda cloning vector with helper phage (ExAssist) as pBK-CMV expression plasmids driven by the powerful immediate early promoter from cytomegalovirus (CMV). The approach to isolating a cDNA clone for IL-XR would involve assaying for radio-labeled IL-X binding in a "null" cell transfected with pools of the NAD-20 cDNA library. Specifically, the cDNA library is plated at a density of ~50,000 plaques/150 mm plate on 20 plates. The phage pools from each plate are eluted in SM buffer and used to obtain pBK-CMV expression plasmid pools using the in vivo excision method applicable to this system. These cDNA "pools" are used to transfect 20 plates of "null" cells. The quantity of radiolabelled IL-X binding to the cells in each plate under normal binding assay conditions is compared to that for an equivalent number of NAD-20 cell and untransfected "null" cell controls. The acquisition of IL-X binding by any plate of "null" cells indicates the presence of a cDNA clone for the IL-XR in the plasmid "pool" used to transfect that plate. The phage that yielded the positive plasmid pool is then plated under lower density (e.g., 10 plates at 5,000 plaques/plate), new plasmids excised from each new, smaller "pool" and the transfection assay repeated. Any positive "pools" are then further diluted and the binding assay repeated until individual plaques can be selected. At this time, pools of 10 or less plasmids can be used to isolate individual clones that encode the IL-XR. Clones can then be assayed in the proliferation bioassay in a transfected "null" cell, since the library screen will rely solely on ligand-binding rather than proliferation bioassay.

(b) Phage Display

The technique developed in the past few years for displaying peptides as fusion proteins on the surface of bacteriophage has enormous potential for screening by a biopanning methodology vast numbers of clones quickly and easily for protein-protein interactions. There are several commercially available systems for use with proteins. Of these, two appear to be reliable and have been used for larger proteins; namely the T7 Select vectors from Novagen (Rosenberg, A. et al. [1996] inNovations 6: 1–6) and the Lambda SurfAZP vector from Stratagene (Amberg, J. et al. [1993] Strategies 5:2–5).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide molecule that encodes a protein, or a biologically active fragment of said protein, that can be obtained from Mycoplasma and is capable of augmenting proliferation of B and T lymphocytes, wherein said protein exhibits a molecular weight of approximately 42 kD on SDS-PAGE.

2. The polynucleotide molecule of claim 1, wherein said polynucleotide comprises the nucleotide sequence shown in SEQ ID NO. 8.

3. The polynucleotide molecule according to claim 1, wherein said polynucleotide comprises the nucleotide sequence shown in SEQ ID NO. 13.

4. The polynucleotide molecule of claim 1, wherein said polynucleotide comprises the nucleotide sequence from nucleotide 198 through nucleotide 1481 of the nucleotide sequence shown in SEQ ID NO. 8.

5. The polynucleotide molecule according to claim 1, wherein said polynucleotide comprises the nucleotide sequence from nucleotide 198 through nucleotide 1481 of the nucleotide sequence shown in SEQ ID NO. 13.

6. The polynucleotide according to claim 1, wherein said polynucleotide comprises nucleotide 270 through nucleotide 1481 of the nucleotide sequence shown in SEQ ID NO. 8.

7. The polynucleotide molecule according to claim 1, wherein said polynucleotide comprises the nucleotide sequence from nucleotide 270 through nucleotide 1481 of the nucleotide sequence shown in SEQ ID NO. 13.

8. The polynucleotide according to claim 1, wherein said protein comprises the amino acid sequence shown in SEQ ID NO. 10.

9. The polynucleotide according to claim 1, wherein said protein comprises the amino acid sequence shown in SEQ ID NO. 11.

10. The polynucleotide according to claim 1, wherein said protein comprises the amino acid sequence shown in SEQ ID NO. 6.

11. The polynucleotide according to claim 1, wherein said protein comprises the amino acid sequence shown in SEQ ID NO. 2.

12. The polynucleotide according to claim 1, wherein said protein comprises the amino acid sequence shown in SEQ ID NO. 14.

13. The polynucleotide according to claim 1, wherein said protein comprises the amino acid sequence shown in SEQ ID NO. 15.

14. An isolated polynucleotide molecule that encodes a protein, or a biologically active fragment of said protein, that can be obtained from Mycoplasma and is capable of augmenting proliferation of B and T lymphocytes, wherein said protein exhibits a predicted molecular weight of approximately 47.7 kD.

15. The polynucleotide molecule of claim 14, wherein said polynucleotide comprises the nucleotide sequence shown in SEQ ID NO. 8.

16. The molecule according to claim 14, wherein said polynucleotide comprises the nucleotide sequence shown in SEQ ID NO. 13.

17. The polynucleotide molecule of claim 14, wherein said polynucleotide comprises the nucleotide sequence from nucleotide 198 through nucleotide 1481 of the nucleotide sequence shown in SEQ ID NO. 8.

18. The polynucleotide molecule according to claim 14, wherein said polynucleotide comprises the nucleotide sequence fromnucleotide 198 through nucleotide 1481 of the nucleotide sequence shown in SEQ ID NO. 13.

19. The polynucleotide according to claim 14, wherein said polynucleotide comprises nucleotide 270 through nucleotide 1481 of the nucleotide sequence shown in SEQ ID NO. 8.

20. The polynucleotide molecule according to claim 14, wherein said polynucleotide comprises the nucleotide sequence from nucleotide 270 through nucleotide 1481 of the nucleotide sequence shown in SEQ ID NO. 13.

21. The polynucleotide according to claim 14, wherein said protein comprises the amino acid sequence shown in SEQ ID NO. 10.

22. The polynucleotide according to claim 14, wherein said protein comprises the amino acid sequence shown in SEQ ID NO. 11.

23. The polynucleotide according to claim 14, wherein said protein comprises the amino acid sequence shown in SEQ ID NO. 6.

24. The polynucleotide according to claim 14, wherein said protein comprises the amino acid sequence shown in SEQ ID NO. 2.

25. The polynucleotide according to claim 14, wherein said protein comprises the amino acid sequence shown in SEQ ID NO. 9.

26. The polynucleotide according to claim 14, wherein said protein comprises the amino acid sequence shown in SEQ ID NO. 16.

* * * * *